United States Patent
Walseth et al.

(10) Patent No.: US 6,593,307 B1
(45) Date of Patent: Jul. 15, 2003

(54) CYCLIC-ADP-RIBOSE ANALOGS

(75) Inventors: Timothy F. Walseth, Roseville, MN (US); Antonio De Flora, Genoa (IT); Elena Zocchi, Genoa (IT); Marina Podesta, Genoa (IT); Long Wong, Roseville, MN (US); Robert A. Aarhus, Coon Rapids, MN (US); Hon Cheung Lee, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 100 days.

(21) Appl. No.: 09/698,611

(22) Filed: Oct. 27, 2000

Related U.S. Application Data

(60) Provisional application No. 60/161,820, filed on Oct. 27, 1999.

(51) Int. Cl.[7] .......................... A61K 31/70; C07H 19/23
(52) U.S. Cl. .............................. 514/47; 514/46; 514/45; 536/26.11
(58) Field of Search ........................ 536/26.11; 514/45, 514/46, 47

(56) References Cited

U.S. PATENT DOCUMENTS

| | | | |
|---|---|---|---|
| 5,486,604 A | 1/1996 | Walseth et al. | 536/26.13 |
| 5,872,243 A | 2/1999 | Gee et al. | 536/26.23 |

OTHER PUBLICATIONS

Clapper, D.L., et al., "Pyridine Nucleotide Metabolites Stimulate Calcium Release from Sea Urchin Egg Microsomes Desensitized to Inositol Trisphosphate", *The Journal of Biological Chemistry*, 262 (20), pp. 9561–9568, (Jul. 15, 1987).

Dargie, P.J., et al., "Comparison of $Ca^{2+}$ mobilizing activities of cyclic ADP–ribose and inositol trisphophate", *Cell Regulation*, 1, pp. 279–290, (Feb. 1990).

Koshiyama, H., et al., "Novel Mechanism of Intracellular Calcium Release in Pituitary Cells", *The Journal of Biological Chemistry*, 266 (26), pp. 16985–16988, (Sep. 15, 1991).

Lee, H.C., "Specific Binding of Cyclic ADP–ribose to Calcium–storing Microsomes from Sea Urchin Eggs", *The Journal of Biological Chemistry*, 266 (4), pp. 2276–2281, (Feb. 5, 1991).

Lee, H.C., et al., "ADP–ribosyl cyclase: an enzyme that cyclized $NAD^+$ into a calcium–mobilizing metabolite", *Cell Regulation*, 2, pp. 203–209, (Mar. 1991).

Lee, H.C., et al., "Structural Determination of a Cyclic Metabolite of $NAD^+$ with Intracellular $Ca^{2+}$–mobilizing Activity", *The Journal of Biological Chemistry*, 264 (3), pp. 1608–1615, (Jan. 25, 1989).

Podesta, M., et al., "Extracellular cyclic ADP–ribose increases intracellular free calcium concentration and stimulates proliferation of human hemopoietic progenitors", *The FASED Journal*, 14, pp. 680–690, (Apr. 2000).

Rusinko, N., et al., "Widespread Occurrence in Animal Tissues of an Enzyme Catalyzing the Conversion of $NAD^+$ into a Cyclic Metabolite with Intracellular $Ca^{2+}$mobilizing Activity", *The Journal of Biological Chemistry*, 264 (20), pp. 11725–11731, (Jul. 15, 1989).

Sowa, T., et al., "The Facile Synthesis of 5'–Nucleotides by the Selective Phosphorylation of a Primary Hydroxyl Group of Nucleosides with Phosphoryl Chloride", *Bulletin of the Chemical Society of Japan*, 48 (7), pp. 2084–2090, (Jul., 1975).

Walseth, T.F., et al., "Determination of endogenous levels of cyclic ADP–ribose in rat tissues", *Biochimica et Biophysica Acta*, 1094, pp. 113–120, (1991).

Walseth, T.F., et al., "Preparation of Cyclic ADP–ribose Antagonists and Caged Cyclic ADP–ribose", *In: Methods in Enzymology, vol. 280, Part J—Vitamins and Coenzymes*, Academic Press, pp. 294–305, (1997).

Wong, L., et al., "Cyclic 3–deaza–adenosine diphosphoribose: a potent and stable analog of cyclic ADP–ribose", *Biochimica et Biophysica Acta*, 1472, pp. 555–564, (1999).

*Primary Examiner*—James O. Wilson
*Assistant Examiner*—Lawrence E Crane
(74) *Attorney, Agent, or Firm*—Schwegman, Lundberg, Woessner & Kluth, P.A.

(57) ABSTRACT

The present invention provides a compound of formula I:

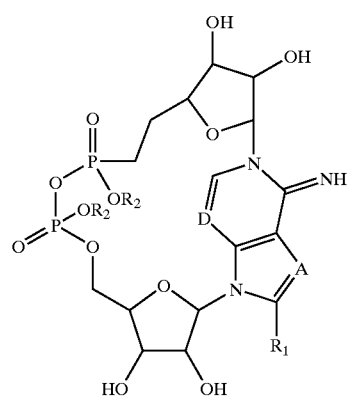

wherein A, D, $R_1$, and $R_2$ are as defined in the specification; or a salt or a detectably labeled derivative thereof. The invention also provides methods of using the compound of formula I or a salt or a detectably labeled derivative thereof for promoting the proliferation of hemopoietic progenitor cells without cell differentiation.

24 Claims, 10 Drawing Sheets

CYCLIC-ADP-RIBOSE ANALOGS

PRIORITY OF INVENTION

This application claims priority from U.S. Provisional Application No. 60/161,820 filed Oct. 27, 1999.

GOVERNMENT FUNDING

The invention described herein was made with government support under Grant Numbers NIDA#11806 and P01-DA08131, awarded by the National Institutes of Health. The United States Government has certain rights in the invention.

BACKGROUND OF THE INVENTION

Cyclic ADP-ribose (cADPR) is a metabolite of $NAD^+$ that is as effective as inositol trisphosphate in mobilizing intracellular $Ca^{+2}$ stores in sea urchin eggs (Clapper, D. L., et al., (1987) *J. Biol. Chem.* 262, 9561–9568; Dargie, P. et al., (1990) Cell Regulation 1, 279–290.) and rat pituitary cells (Koshiyama, H., et al., (1991) *J. Biol. Chem.* 266, 16985–16988.). The metabolite itself (Walseth, T. F., Aarhus, R., et al., (1991) *Biochim. Biophys. Acta* 1094, 113–120) as well as its synthesizing enzyme, ADP ribosyl cyclase (Rusinko, N. and Lee, H. C. (1989) *J. Biol. Chem.* 264, 11725–11731; Lee, H. C. and Aarhus, R. (1991) *Cell Regulation* 2, 203–209) are present in various mammalian and invertebrate tissues. The cyclic structure of the metabolite is formed by linking the adenine group of $NAD^+$ to the terminal ribosyl unit and displacing the nicotinamide moiety (Lee, H. C., et al., (1989) *J. Biol. Chem.* 264, 1608–1615). The $Ca^{+2}$ release mechanism that is activated by cADPR is totally distinct from the inositol trisphosphate pathway. It is insensitive to blockage by heparin, a competitive inhibitor of the receptor for inositol trisphosphate. Furthermore, inositol trisphosphate was shown to complete at least a thousand times less effectively than cADPR for the specific microsomal binding site for cADPR (Lee, H. C. (1991) *J. Biol. Chem.* 266, 2276–2281).

Several observations indicate involvement of cADPR in the calcium-controlled events taking place during the process of egg fertilization, completion of the oocyte meiotic cycle and the first stages of cell division in invertebrates. Moreover, oscillations of ADP-ribosyl cyclase activity and of cADPR concentration during cell cycle progression have also been reported in the unicellular protist *Euglena gracilis*. These observations point to an ancient evolutionary role of cADPR as a calcium-releasing signal involved in the control of cell proliferation.

In vertebrates, cADPR has been identified in most tissues and two ADP-ribosyl cyclases, CD38 and BST-1, have been described so far: CD38 is a type II transmembrane glycoprotein, while BST-1 is a glycosyl-phosphatidylinositol-anchored protein. Both are bifunctional ectoenzymes, catalyzing the synthesis and hydrolysis of cADPR at their ectocellular domain. The widespread tissue distribution of cADPR in mammals suggests a role for this nucleotide in calcium-controlled, tissue-specific cell functions, which include secretion, contraction, cell proliferation and apoptosis. Indeed, extracellularly added cADPR has been demonstrated to release calcium from ryanodine-sensitive intracellular stores in a wide range of permeabilized cell types and to elicit tissue-specific functional responses in permeabilized P-pancreatic cells, smooth muscle myocytes and oocytes. cADPR has also been shown to increase cytokine-induced B-lymphocyte proliferation and to increase the depolarization-induced elevation of the intracellular free calcium concentration ($[Ca^{2+}]_i$) in cerebellar neurons.

Recently, "de novo" expression of CD38 in $CD38^-$ cells was demonstrated to induce a shortening of the cell cycle, an effect which was shown to be causally related to the intracellular production of cADPR and to the consequent increase of the $[Ca^{2+}]_i$. This observation suggests that cADPR may play a role in the regulation of cell cycle progression.

Currently, there is a need for improved methods and agents useful for promoting the proliferation of hemopoietic progenitor cells without cell differentiation. In particular there is a need for agents that are more potent or more stable to heat and degradation (e.g. enzymatic degradation) than known agents such as cyclic ADP ribose (cADPR). There is also a need for agents that are useful to mobilize intracellular calcium. As well as a need for agents that act as antagonists of cADPR and cADPR induced calcium release.

SUMMARY OF THE INVENTION

The present invention provides compounds and methods that are useful for promoting the proliferation of hemopoietic progenitor cells without cell differentiation. Accordingly, the invention provides a compound of formula I:

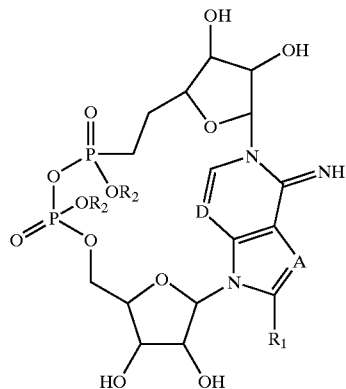

wherein:

A is —N═, or —C(H)═;

D is —C(H)═;

$R_1$ is hydrogen, amino, azido, or halo; and each $R_2$ is independently hydrogen, or a suitable photolabile caging group;

or a salt or a detectably labeled derivative thereof.

Certain compounds of formula I (e.g. compounds wherein $R_1$ is hydrogen) may be particularly useful to mobilize intracellular calcium. Other compounds of the invention (e.g. compounds wherein $R_1$ is amino, azido or halo) may be particularly useful as stable antagonists of cADPR and cADPR induced calcium release. Representative compounds of formula (I) (e.g. compounds wherein D is —C(H)═) have been found to be more stable to heat and degradation (e.g. enzymatic degradation) than corresponding cADPR analogs.

Additionally, the invention provides a method for promoting the proliferation of a hemopoietic progenitor cell comprising contacting the cell with a compound of the invention.

The invention also provides pharmaceutical compositions comprising a compound of formula I and a pharmaceutically acceptable carrier.

The invention also provides processes and intermediates disclosed herein that are useful for preparing compounds of the invention.

The invention also provides a method to antagonize cADPR induced calcium release in a cell comprising contacting the cell with a compound of formula (I) or a salt thereof.

The invention also provides a method to promote the proliferation of a lymphocyte comprising contacting the lymphocyte with a compound of formula (I) or a salt thereof.

The invention also provides a method to enhance the immune system of a mammal comprising administering to a mammal in need of such treatment, an amount of a compound of formula (I) or a salt thereof.

The invention also provides a method to treat cancer comprising administering to a mammal in need of such treatment, an amount of a compound of formula (I) or a salt thereof.

The invention also provides a method to treat a disease where reduced immune system function is implicated and improved immune system function is desired comprising administering to a mammal in need of such therapy an amount of a formula (I) or a salt thereof.

BRIEF DESCRIPTION OF THE FIGURES

FIG. 9A is a trace from a representative experiment showing the effect on $[Ca^{2+}]_i$ of the addition of 100 $\mu$M cADPR to digitonin-permeabilized CB MNC.

DETAILED DESCRIPTION OF THE INVENTION

Figure 1:
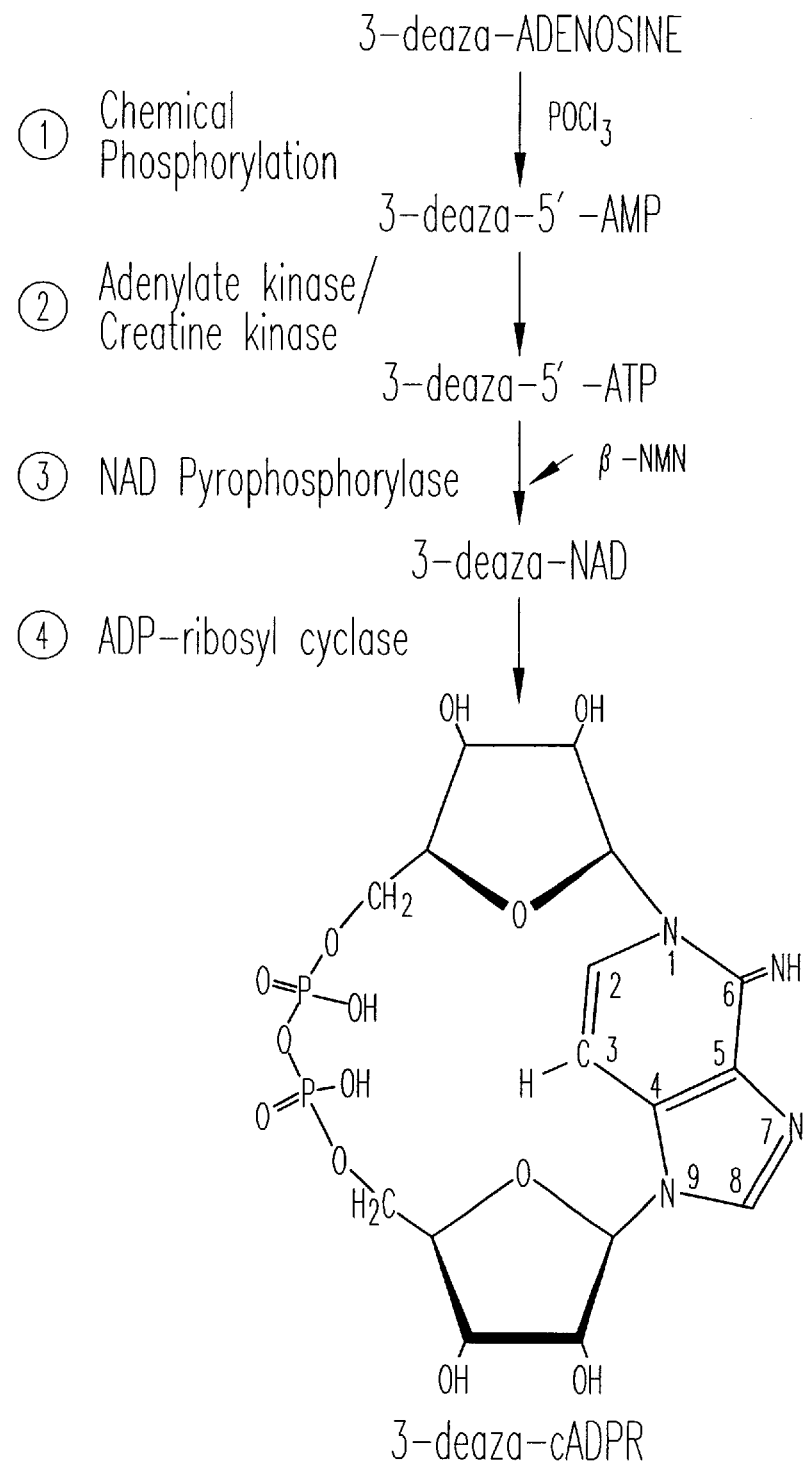
FIG. 1: The synthesis and structure of 3-deaza-cADPR. 3-deaza-cADPR was synthesized from 3-deaza-adenosine by a four-step chemical/enzymatic procedure. Step 1 involves chemical phosphorylation of 3-deaza-adenosine with phoshoryl chloride. In step 2, 3-deaza-5'-AMP is enzymatically converted to 3-deaza-5'-ATP by the combined actions of adenylate kinase and creatine kinase. The 3-deaza-5'-ATP is converted to 3-deaza-NAD with NAD pyrophosphorylase in step 3. The 3-deaza-NAD is converted to 3-deaza-cADPR with Aplysia ADP-ribosyl cyclase in step 4. 3-deaza-cADPR differs from cADPR by substitution of a carbon for nitrogen at the 3 position of the adenine ring.

The following definitions are used, unless otherwise described: halo is fluoro, chloro, bromo, or iodo.

Suitable photolabile caging groups include groups having the properties described in U.S. Pat. No. 5,872,243 (e.g. an ortho-nitrobenzyl group).

Suitable detectably labeled derivatives of compounds of formula I include compounds of formula I comprising one or more detectable radionuclide. Such radionuclides can be incorporated into the structure of formula I, or can be appended to a compound of formula I. For example, $^{32}P$, $^{33}P$ or $^{14}C$ can be incorporated at any synthetically feasible position in a compound of formula I, or $^3H$ can be incorporated at any non-exchangeable position.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine cADPR agonist or antagonist activity using the standard tests described herein, or using other similar tests which are well known in the art.

Processes for preparing compounds of formula I or for preparing intermediates useful for preparing compounds of formula I are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. Preferred salts for administration to mammals are pharmaceutically acceptable salts.

The ability of a compound of the invention to mobilize intercellular calcium or to antagonize cADPR induced calcium release may be determined using pharmacological models which are well known to the art (for example, see U.S. Pat. No. 5,486,604), or using the assays described hereinbelow.

The following abbreviations and words are used herein: cADPR, cyclic adenosine diphosphoribose: 3-deaza-cADPR, cyclic 3-deaza-adenosine diphosphoribose; IM, intracellular medium; TEAB, triethylammonium bicarbonate; CICR, calcium-induced calcium release; and P-NMN, beta-nicotinamide mononucleotide.

Representative compounds of formula (I) have also been found to promote the proliferation of lymphocytes. The ability of a compound to promote the proliferation of lymphocytes can be determined using assays that are known in the art. As a result, the invention provides a method to promote the proliferation of a lymphocyte (in vitro or in vivo) comprising contacting the lymphocyte with a compound of the invention.

As a result of their ability to promote the proliferation of lymphocytes (e.g. T-lymphocytes or B-lymphocytes) compounds of the invention are also useful for enhancing (e.g. improving, or causing a stronger immune response than what would be expected in the absence of the influence of a compound of the invention) the immune system of a mammal. Accordingly, the invention provides a method to enhance the immune system of a mammal comprising administering to a mammal in need of such treatment, an amount of a compound of the invention effective to promote the proliferation of lymphocytes.

Additionally, weakening of the immune system can result from various diseases or pathologies (e.g. AIDS), or as a result of aging. Compounds of the invention that are capable of promoting the proliferation of lymphocytes, and thus enhancing immune function, can be used to treat diseases associated with reduced immune function, such as AIDS. Thus, the invention provides a method to treat a disease where a suppressed, compromised, or reduced immune system function is implicated (e.g., AIDS) and improved immune system function is desired, comprising administering to a mammal in need of such therapy an amount of a compound of the invention effective to promote the proliferation of lymphocytes.

Weakening of the immune system is also an unwanted side effect of many cancers and cancer therapies. For example, the use of radiation therapy or certain chemotherapeutic agents for the treatment of cancer, can produce a detrimental supression or reduction in immune function or response. As a result, the patient can become more susceptible to viral, bacterial or fungal infection. Thus, the invention also provides a method to treat cancer comprising administering to a mammal in need of such therapy an amount of a compound of the invention effective to promote the proliferation of lymphocytes. The invention also provides a method to treat cancer comprising administering radiation therapy or chemotherapy to a mammal in combination with an amount of a compound of the invention effective to promote the proliferation of lymphocytes.

EXAMPLES

Example 1

Synthesis of the 3-deaza-adenine analog of cADPR

Synthesis of cyclic 3-deaza-adenosine diphosphoribose (3-deaza-cADPR)

3-deaza-cADPR was synthesized from 3-deaza-adenosine by a combination of chemical and enzymatic steps (see FIG. 1). The 3-deaza-adenosine was first chemically phosphorylated to 3-deaza-adenosine 5'-monophosphate (3-deaza-5'-AMP), which was converted to 3-deaza-cADPR by a series of enzymatic reactions using adenylate kinase, creatine kinase, NAD pyrophosphorylase and Aplysia ADP-ribosyl cyclase. The details of each step are described below.

Synthesis of 3-deaza-5'-AMP 3-deaza-adenosine was chemically phosphorylated by the method of Sowa and Ouchi (Sowa, T. and Ouchi, S. (1975) Bull. Chem. Soc. Japan 48, 2084–2090). 3-deaza-adenosine (6.3 mg) was added to a stirred mixture containing 41 μl of phosphoryl chloride, 5 μl of water, 39 μl of pyridine and 99 μl of acetonitrile. The reaction was allowed to proceed for four hours on ice. At this point, 1 ml of cold water was added and the reaction stirred for an additional hour on ice. The reaction was then diluted with water to 3 ml and neutralized to pH 9 by adding 5 N NaOH. The 3-deaza-5'-AMP was purified by phenylboronate chromatography using a 0.6×4 cm column of PBA-60 (Walseth, T. F., et al., (1988) Methods in Enzymol. 159, 60–74). The sample was first diluted to 10 ml through the addition of a buffer containing 200 mM triethylammonium bicarbonate and 10 mM $MgCl_2$ (TEAB/Mg buffer). The diluted sample was slowly added to the PBA-60 column in 2 ml aliquots. The column was then washed sequentially with 6 ml of TEAB/Mg (2 ml/wash) and 1 ml of water. The 3-deaza-5'-AMP was eluted by washing with an additional 10 ml of water. The 3-deaza-5'-AMP fraction was collected and evaporated to dryness using a Savant Speed-Vac concentrator. The PBA-60 column effectively removed inorganic phosphate from the 3-deaza-5'-AMP product. The 3-deaza-5'-AMP was further purified by anion-exchange chromatography using a 1×10 cm column packed with AG MP-1 resin. The column was eluted at 4 ml/min using a concave upward gradient of trifluoroacetic acid (TFA) from 1.5 to 150 mM over 30 minutes. The 3-deaza-5'-AMP was collected and evaporated to dryness. The yield of 3-deaza-5'-AMP through the two purification steps was 3.5 mg (56%).

Conversion of 3-deaza-5'-AMP to 3-deaza-5'ATP

The 3-deaza-5'-AMP (3.5 mg) was reconstituted in a total volume of 6 ml with a solution containing the final concentrations of the following reagents: 10 mM Tris-HCl, pH 7.5, 10 mM creatine phosphate, 10 mM $MgCl_2$, 0.3 mM dATP, 100 μg/ml creatine kinase and 1 mM DTT. The reaction was initiated by adding 60 μl of 5 mg/ml adenylate kinase and allowed to incubate for 16 hours at 37° C. The resulting 3-deaza-5'-ATP was purified on a Bio-RAD Bio-Scale Q2 column. The column was eluted with a gradient of triethylammonium bicarbonate, pH 8.8 from 0 to 1M at a flow rate of 2 ml/min over 30 minutes. Four runs using 1.5 ml of sample per run were used in purification of the sample. The 3-deaza-5'-ATP peaks were pooled and purified by PBA-60 chromatography as described above. The sample pool was adjusted to a final concentration of 10 mM $MgCl_2$ and applied to a 0.6×4 cm column of PBA-60. The column wash and elution procedures were as described above. The PBA-60 purification step was used to insure that dATP was completely separated from 3-deaza-5'-ATP. The water fraction containing 3-deaza-5'-ATP was evaporated to dryness and stored at −20° C. The enzymatic conversion of 3-deaza-5'-AMP to 3-deaza-5'-ATP proceeded with a yield of over 90%. dATP was initially used in the conversion of 3-deaza-5'-AMP to 3-deaza-5'-ATP because it was easily separated from 3-deaza-5'-ATP by phenylboronate chromatography. In subsequent preparations, 3-deaza-5'-ATP was used instead of dATP and the PBA-60 chromatography step was eliminated.

Synthesis of 3-deaza-NAD 3-deaza-5'-ATP was reconstituted in 7 ml of a solution containing the final concentrations of following reagents; 10 mM Tris-HCl, pH 7.5, 5 mM β-NMN, 10 mM $MgCl_2$, 2 mM DTT, 2 mM creatine phosphate, 0.05 U/ml inorganic pyrophosphatase, 50 μg/ml creatine kinase and 25 μg/ml adenylate kinase. The final concentration of 3-deaza-5'-ATP was usually between 1 and 4 mM. The conversion to 3-deaza-NAD was initiated by adding 50 μl of 10 mg/ml NAD pyrophosphorylase and the reaction allowed to incubate at 37° C. for 6 to 16 hours. The reaction proceeds to completion with all 3-deaza-5'-ATP converted to 3-deaza-NAD. The 3-deaza-NAD was purified by AG MP-1 chromatography as described above. The purified product was evaporated to dryness before conversion to 3-deaza-cADPR.

Conversion of 3-deaza-NAD to 3-deaza-cADPR 3-deaza-NAD stocks were diluted to 0.5 mM with 10 mM Tris-HCl, pH 7.5. The diluted stocks were incubated with Aplysia ADP-ribosyl cyclase (final concentration of 0.1 μg/ml) for 2 hours at room temperature. The resulting 3-deaza-cADPR was purified by AG MP-1 chromatography as described above. The purified 3-deaza-cADPR was evaporated to dryness and stored at −20° C.

Synthesis of 7-deaza-cADPR 7-deaza-cADPR was synthesized by the methods described above for 3-deaza-cADPR except the starting material was 7-deaza-5'-AMP and thus the chemical phosphorylation step was unnecessary.

Spectral characterization of 3-deaza-cADPR

The molar extinction coefficient of 3-deaza-cADPR was determined by total phosphate analysis using NADP as a standard. The $\epsilon_M$ at $\lambda_{max}$ was 11251±1215 $M^{-1}$ $cm^{-1}$ (n=6). The $^1H$ spectrum of 3-deaza-cADPR was obtained using a 500 MHz spectrometer (Lee, H. C., et al., (1989) J. Biol. Chem. 264, 1608–15). The 3-deaza-cADPR (about 1 μmole) used for the NMR studies was eluted from an AG MP-1 column, lyophilized and reconstituted with $D_2O$.

$Ca^{2+}$ Release Assays

Homogenates (1.25%) of Strongylocentrotus purpuratus eggs were prepared as described previously (Walseth, T. F., et al., (1997) Methods in Enzymol. 280, 294–305). Briefly, 25% homogenates were diluted with an intracellular medium (IM) consisting of 250 mM potassium gluconate buffer (pH 7.2), 0.5 mM ATP, 4 mM creatine phosphate, 2 units/ml creatine kinase, and 3 μM fluo-3. The dilutions and all experiments were conducted at 17° C. Free $Ca^{2+}$ concentrations were measured by monitoring the fluorescence (490 nm excitation, 535 nm emission) of the indicator using a Perkin Elmer Model 650 spectrofluometer. The experiments were performed by adding 200 μl of the 1.25% homogenate to a cuvette containing a magnetic stir bar. Samples were added in 1–5 μl aliquots. For some experiments a BMG FluoStar 96 well fluorescence plate reader was used. In this case, samples to be tested were added to wells of a 96 well plate in 1.5 μl aliquots. Calcium release was initiated by adding 150 μl of homogenate to each well with a multichannel pipette. Six to eight wells were measured simultaneously. Samples to be tested were diluted in IM buffer containing 10 μM EGTA.

Microinjection of L. pictus eggs

Eggs were microinjected with 3-deaza-cADPR as described previously (Lee, H. C., Aarhus, R., and Walseth, T. F. (1993) Science 261, 352–355), except that fluo-3 was used as the calcium indicator. Injection volumes ranged from 0.5 to 1.5% of the egg volume and were used in the calculation of the final 3-deaza-cADPR concentration within the egg.

Materials

Trifluoroacetic acid, 3-deaza-adenosine, 7-deaza-adenosine 5'-monophosphate, dATP, phosphoryl chloride and Aplysia ADP-ribosyl cyclase were purchased from Sigma Chemical Co. (St. Louis, Mo.). Recombinant CD38 was expressed in a yeast system and purified as previously described (Munshi, C. B., et al., (1997) Methods in Enzymol. 280, 318–30). Cyclic ADP-ribose was synthesized using Aplysia ADP-ribosyl cyclase as previously described. AG MP-1 resin and the Bio-Scale Q2 column were purchased from Bio-Rad (Hercules, Calif.). Adenylate kinase, NAD-pyrophosphorylase, creatine phosphokinase, and creatine phosphate and were obtained from Boehringer Mannheim (Indianapolis, Ind.). Sequence grade inorganic pyrophosphatase was from United States Biochemical Inc. PBA-60 was supplied by Amicon. All other reagents were of the highest grade available.

Results

Results show that modification of the 3-position of the adenine ring (nitrogen to carbon) dramatically increases the $Ca^{2+}$ releasing activity by as much as 70 times. In addition, 3-deaza-cADPR is resistant to both heat and enzymatic hydrolysis.

FIG. 1 summarizes the strategy used for the synthesis of 3-deaza-cADPR. 3-deaza-5'-AMP was synthesized by selectively phosphorylating the 5'-hydroxyl of 3-deaza-adenosine. Previous schemes to produce cADPR analogs have utilized various carbodiimide coupling methods to synthesize NAD analogs from the AMP analogs. However, these chemical coupling procedures are often plagued by low yields and the production of multiple contaminating products. 3-deaza-5'-AMP was found to be a substrate for adenylate kinase and 3-deaza-5'-ATP can be formed in high yields using a combination of this enzyme and creatine kinase. In addition, 3-deaza-5'-ATP was found to be a good substrate for NAD pyrophosphorylase. Thus, 3-deaza-NAD is readily synthesized from 3-deaza-5'-AMP enzymatically and in high yield. The ADP-ribosyl cyclase from *Apylsia ovotestis* is promiscuous, using various NAD analogs as substrates (Bailey, V. C., et al., (1996) FEBS Lett. 379, 227–230; Bailey, V. C., et al., (1997) Chem. Biol. 4, 51–61; Graeff, R. M., et al.,(1994) J. Biol. Chem. 269, 30260–7; and Graeff, R. M., et al., (1996) Biochemistry 35, 379–86). 3-Deaza-NAD also proved to be a good substrate for this enzyme. Thus, the invention provides a method for preparing 3-deaza-NAD comprising contacting 3-deaza-5'-AMP with a suitable enzyme to provide the 3-deaza-NAD.

Figure 2A:
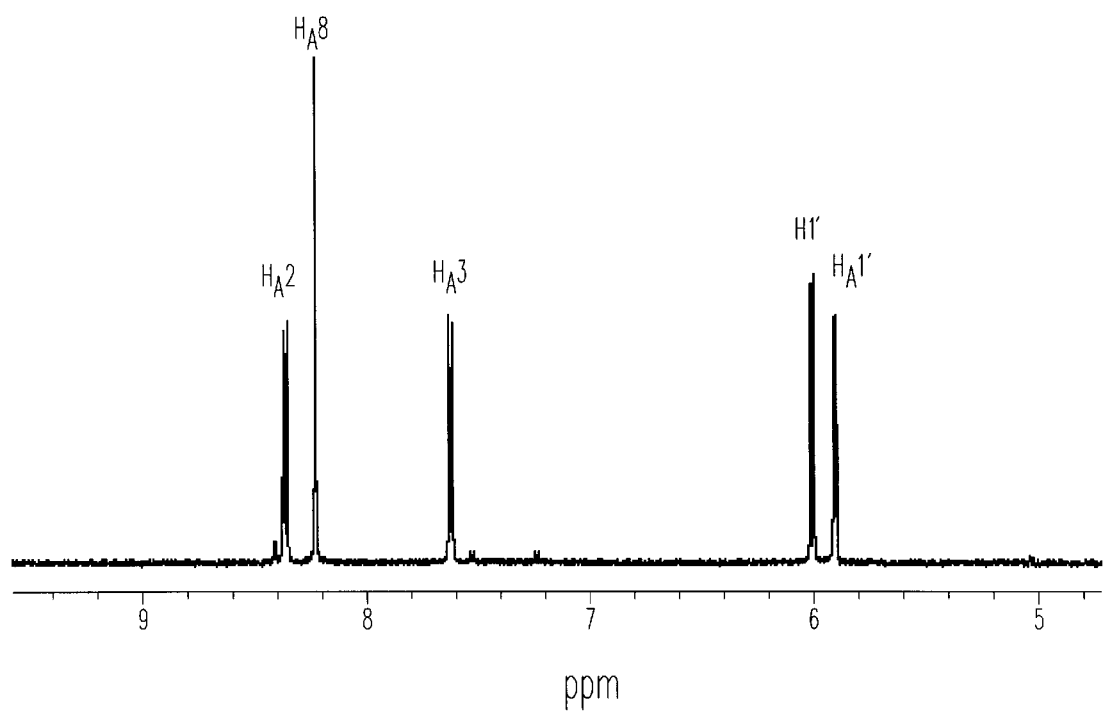
FIG. 2. Spectral characterization of 3-deaza-cADPR. A. 500 MHz proton NMR spectrum of 3-deaza-cADPR. The region below 5 ppm has been deleted because of interference in this region by water. All peaks shown integrate to 1 proton. Peaks labeled $H_A2$, $H_A8$ and $H_A3$ correspond to the 2, 8 and 3 protons on the 3-deaza-adenine ring, respectively. Peaks labeled H1' and $H_A1$ correspond to the anomeric carbons of the N1-adeninyl 1 ribose and N9-adeninyl ribose, respectively. B. UV spectra of 3-deaza-NAD (closed circles) and 3-deaza-cADPR (open circles). Both spectra were obtained in 10 mM Tris-HCl, pH 7.5.

The structure of 3-deaza-cADPR is shown in FIG. 1. The proton NMR of 3-deaza-cADPR displays the expected protons for a 3-deaza-adenine ring between 7.6 and 8.2 ppm (FIG. 2A). The assignments of the protons at the 2 and 3 positions of the 3-deaza-adenine ring and the anomeric protons of the ribose moieties are based on published NMR data for 3-deaza-adenosine and cADPR, respectively. One difference between 3-deaza-cADPR and cADPR is the absence of the 2'-proton of the N9 adeninyl ribose at about 5.2 ppm. This proton is shifted downfield by an interaction with the nitrogen at N3 of the adenine ring in cADPR (Wada, T., et al., (1995) Nucleosides Nucleotides 14, 1301–1314). This interaction is not possible in 3-deaza-cADPR.

Figure 2B:
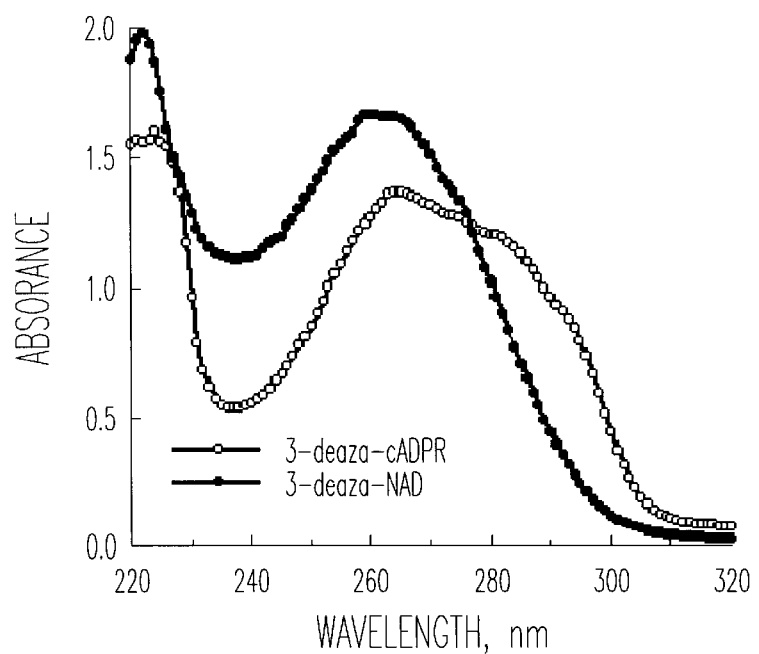

The UV spectra of 3-deaza-NAD and 3-deaza-cADPR are shown in FIG. 2B. The spectrum of 3-deaza-NAD displays a $\lambda_{max}$ of 263 nm, which is similar to other 3-deaza-adenine nucleotides. Conversion to 3-deaza-cADPR is associated with a shift towards higher wavelengths. 3-deaza-cADPR has a $1_{max}$ of 265 nm and a prominent shoulder at about 280 nm. The $e_M$ of 3-deaza-cADPR was determined by total phosphate analysis and was found to be 11251±1215 (n=6) $M^{-1}$ $cm^{-1}$.

Figure 3A:
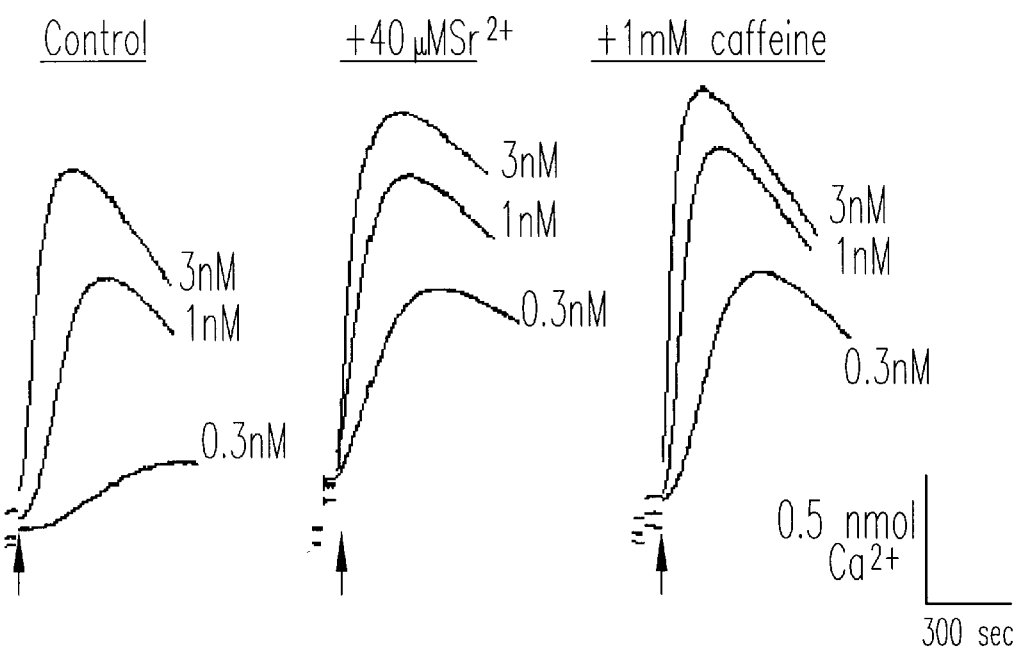
FIG. 3: Calcium release properties of 3-deaza-cADPR.
A. $Ca^{2+}$ release induced by increasing concentrations of 3-deaza-cADPR. Left column of traces show $Ca^{2+}$ release in response to increasing concentrations of 3-deaza-cADPR. Middle column of traces show $Ca^{2+}$ release with 3-deaza-cADPR in the presence of 40 $\mu$M $Sr^{2+}$. Right column traces show $Ca^{2+}$ release with 3-deaza-cADPR in the presence of 1 mM caffeine.
B. Left, middle and right column of traces similar to those in panel A except cADPR was used. Arrows indicate the time of addition of 3-deaza-cADPR or cADPR.
C. Left trace: The addition of 1 $\mu$M cADPR desensitizes the egg homogenate system to a subsequent challenge with 500 nM 3-deaza-cADPR. Right trace: The addition of 500 nM 3-deaza-cADPR desensitizes the system to subsequent challenge by 1 $\mu$M cADPR.
D. 8-amino-cADPR blocks the $Ca^{2+}$ release stimulated by 3-deaza-cADPR. The final concentration of 3-deaza-cADPR for each trace is 2.7 nM. The final concentrations of 8-amino-cADPR are indicated on the figure.
Figure 3B:
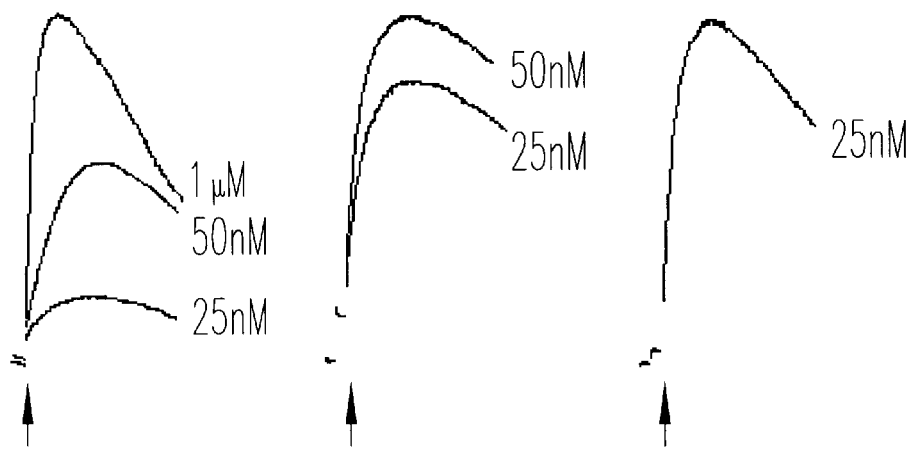

$Ca^{2+}$ Release Properties of 3-deaza-cADPR. The effects of 3-deaza-cADPR on $Ca^{2+}$ release from sea urchin egg homogenates are shown in FIGS. 3 and 4. 3-deaza-cADPR induces $Ca^{2+}$ release with properties very similar to cADPR (FIGS. 3 A, B, C). Final concentrations of 3-deaza-cADPR as low as 0.3 nM were able to elicit $Ca^{2+}$ mobilization (FIG. 3A, control). Concentrations of cADPR around 25 nM are needed to induce $Ca^{2+}$ release (FIG. 3B, control), thus 3-deaza-cADPR may be more potent than cADPR.

cADPR-induced calcium release is potentiated by divalent cations such as $Sr^{2+}$ and caffeine (Lee, H. C., et al., (1994) Nature 370, 307–9). FIG. 3B shows that the prior addition of 40 $\mu M$ $Sr^{2+}$ or 1 mM caffeine to the egg homogenate, enhances the ability to 25 nM cADPR to induce $Ca^{2+}$ release. Similar potentiation of the $Ca^{2+}$ release activity of 3-deaza-cADPR (0.3 nM) by $Sr^{2+}$ and caffeine is shown in FIG. 3A.

Figure 3C:
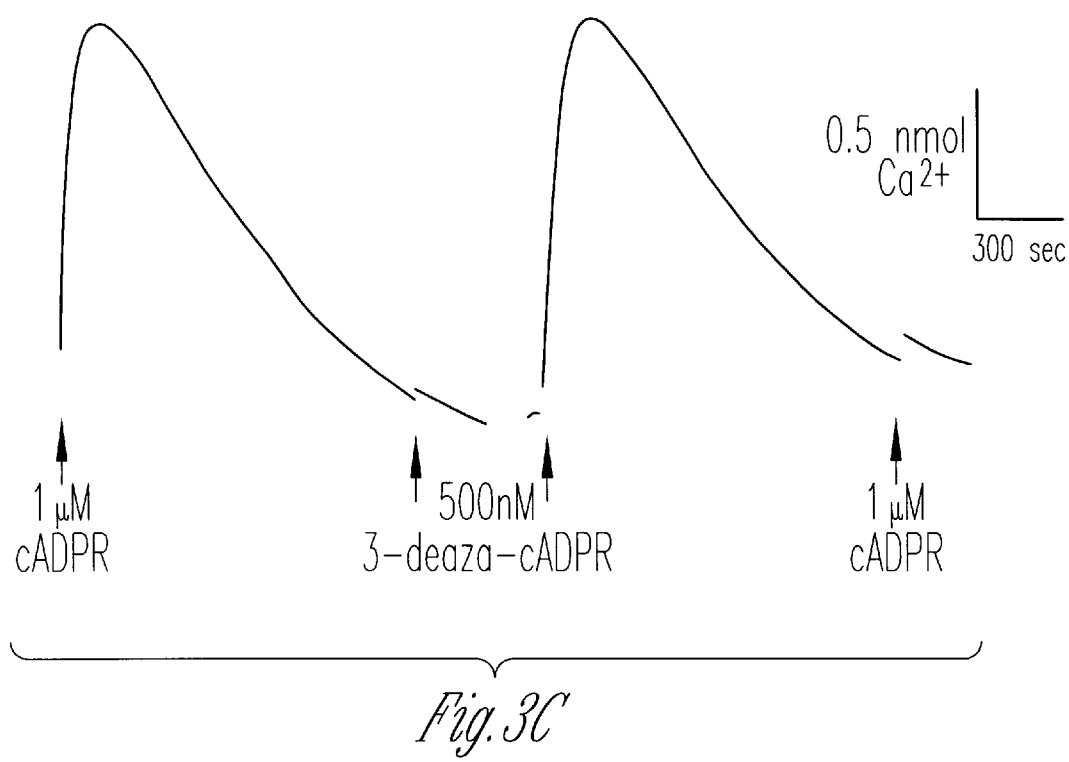
Figure 3D:
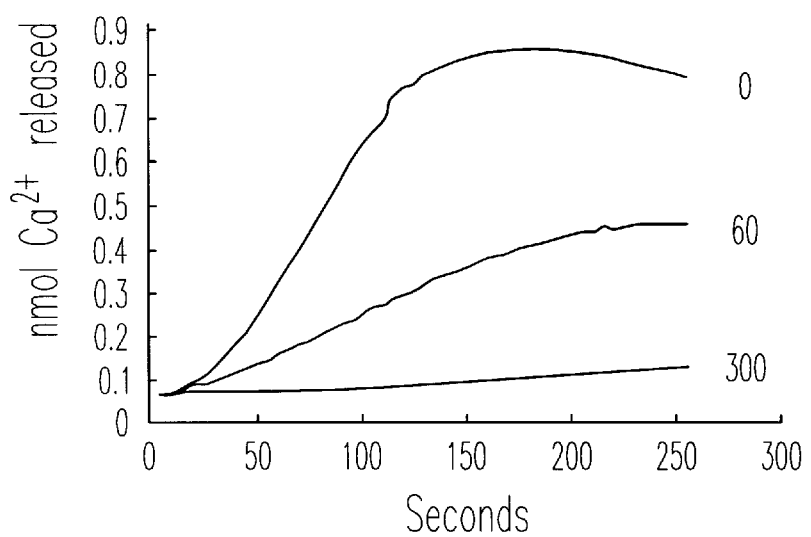
Figure 4:
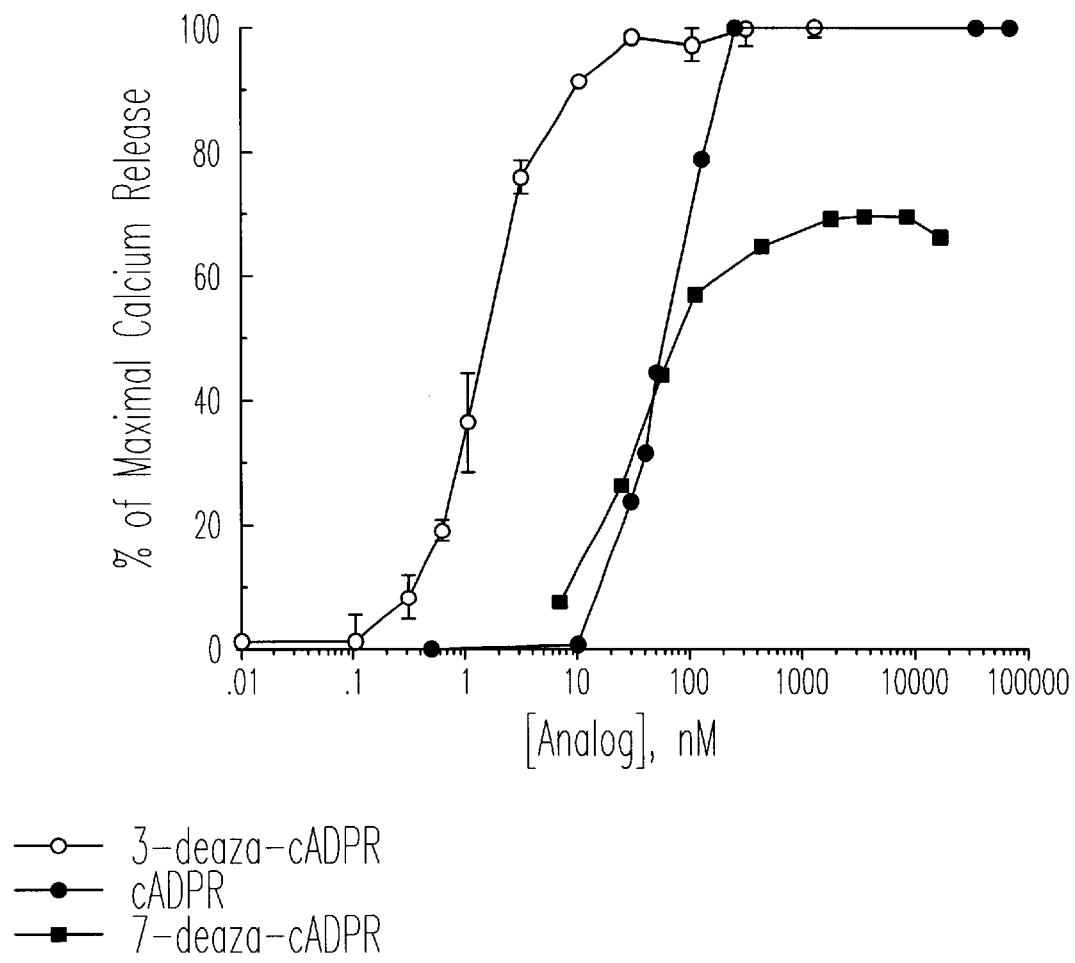
FIG. 4: Concentration-response curves for cADPR (closed circles), 3-deaza-cADPR (open circles) and 7-deaza-cADPR (open squares). Calcium release induced by analogs are compared to that elicited by 30 $\mu$M cADPR (100%). The 3-deaza-cADPR data is taken from a representative experiment performed in triplicate. The error bars are standard deviations. The cADPR and 7-deaza-cADPR data are from a representative experiment performed in duplicate.

FIG. 3C shows that cADPR and 3-deaza-cADPR can desensitize each other. A high concentration of cADPR (1 $\mu M$) induces maximal $Ca^{2+}$ release from the homogenates, which desensitizes and fails to respond to the subsequent addition of 500 nM 3-deaza-cADPR. Likewise, 500 nM 3-deaza-cADPR renders the system unresponsive to a later challenge by 1 $\mu M$ cADPR (FIG. 3C). FIG. 3D shows that 8-amino-cADPR, a selective antagonist of the cADPR system, can also inhibit 3-deaza-cADPR-induced $Ca^{2+}$ release. The inhibitory effect of 8-amino-cADPR is better at 300 nM than at 60 nM. The data presented in FIG. 3 confirm that 3-deaza-cADPR releases $Ca^{2+}$ through the same mechanism used by cADPR.

An interesting feature of the $Ca^{2+}$ release induced by 3-deaza-cADPR is that, at low concentrations, an appreciable lag is seen before $Ca^{2+}$ release takes place (FIG. 3A). The lag time before release is shortened as the concentration of 3-deaza-cADPR is increased, (FIG. 3A, control). This behavior is not observed with cADPR. It is possible that the lag represents a binding event that is slower with 3-deaza-cADPR than with ADPR.

FIG. 4 shows the concentration-responses for 3-deaza-cADPR and ADPR. The half-maximal concentrations for $Ca^{2+}$ release are 1.0±0.4 nM (n=3) for 3-deaza-cADPR and 70 nM for cADPR. Thus, 3-deaza-cADPR is 70 times more potent than cADPR in releasing $Ca^{2+}$. Also compared is the concentration-response of another deaza analog of cADPR, 7-deaza-cADPR. This analog is capable of releasing only about 70% of the $Ca^{2+}$ release induced by either cADPR or 3-deaza-cADPR (FIG. 4), confirming that it is a partial agonist as previously reported. The $EC_{50}$ value for 7-deaza-cADPR is about 25 nM in the *S. purpuratus* system and more potent than cADPR ($EC_{50}$=70 nM). This differs somewhat from the data obtained with *L. pictus,* where cADPR is more potent than 7-deaza-cADPR (Bailey, V. C., et al., (1997) Chem. Biol. 4, 51–61).

Figure 5A:
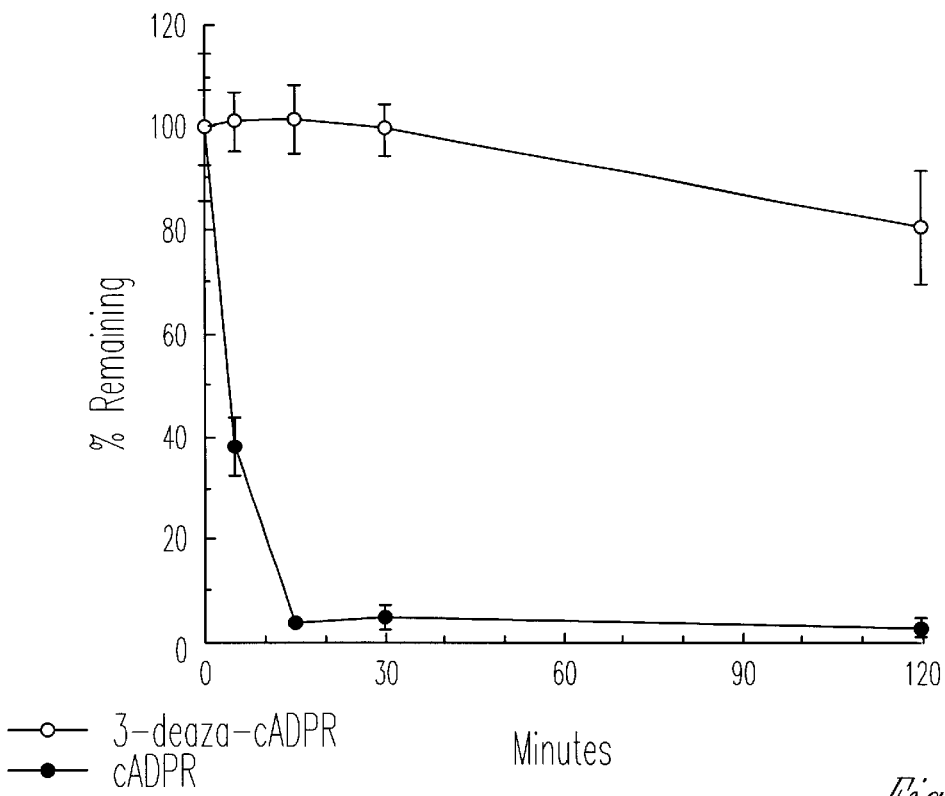
FIG. 5: Stability of 3-deaza-cADPR and cADPR.
A. cADPR (1 $\mu$M, closed circles) and 3-deaza-cADPR (350 nM, open circles) were incubated in a boiling water bath for the indicated times. Aliquots were then cooled on ice and the ability of the sample to release $Ca^{2+}$ determined. Data is average±sd for a representative experiment performed in triplicate.
B. cADPR (1 $\mu$M, closed circles) and 3-deaza-cADPR (350 nM, open circles) were incubated with 1 $\mu$g/ml CD38 at 37° C. for the indicated times. $Ca^{2+}$ release was assayed immediately by diluting an aliquot of the reaction mixture 100-fold into the assay system. Data presented are averages of a representative experiment performed in duplicate.
Figure 5B:
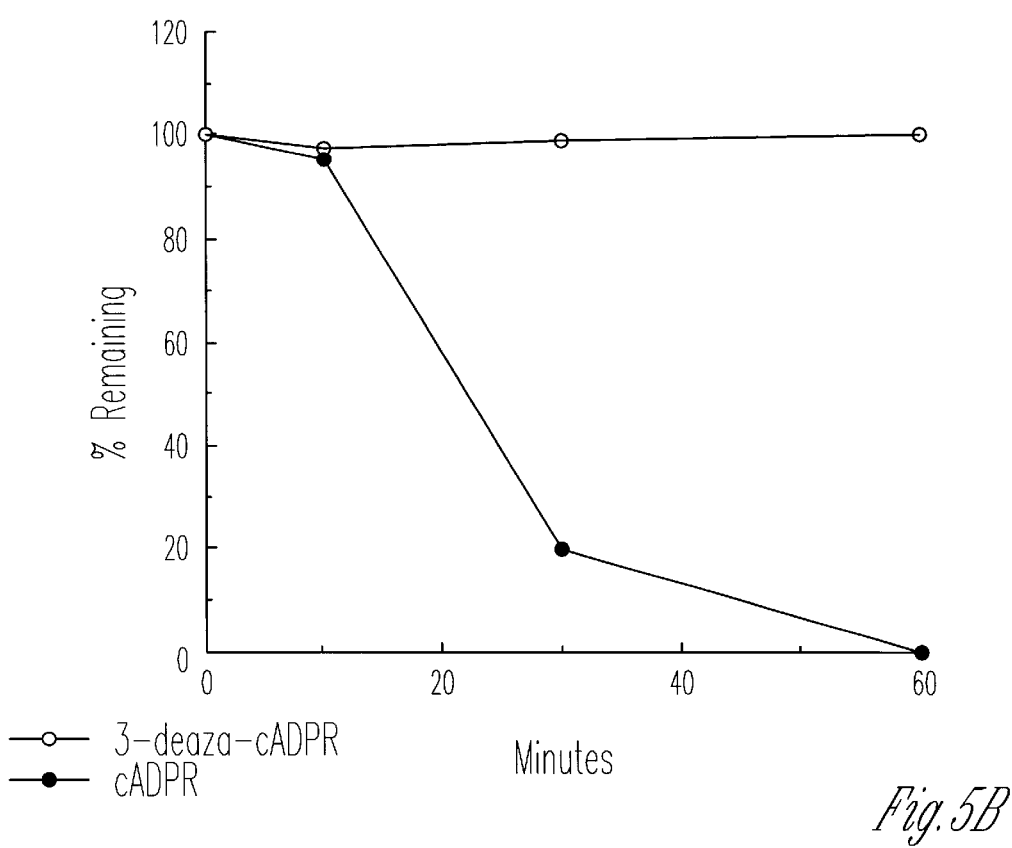

An interesting property of 7-deaza-cADPR is that the N1-glycosidic linkage of this nucleotide is resistant to hydrolysis. Whether 3-deaza-cADPR exhibits similar resistance to hydrolysis was investigated. 3-deaza-cADPR and cADPR were incubated in either a boiling water bath (FIG. 5A) or with CD38 (FIG. 5B), an enzyme that readily hydrolyzes cADPR (Mehta, K., Shahid, U., and Malavasi, F. (1996) FASEB J. 10, 1408–1417). At the indicated times, aliquots were removed and assayed for their ability to release $Ca^{2+}$. The ability of cADPR to induce $Ca^{2+}$ release was virtually eliminated by boiling for 15 minutes (FIG. 5A). This treatment has been shown to rapidly hydrolyze cADPR to ADPR. In contrast, only about 15% of the 3-deaza-cADPR was inactivated upon boiling for up to two hours (FIG. 5A). Similarly, under the conditions employed, CD38 completely hydrolyzed cADPR, whereas this enzyme did not hydrolyze 3-deaza-cADPR (FIG. 5B). HPLC analyses of both the boiled and the CD38 treated samples confirmed the stability of 3-deaza-cADPR (data not shown). These results indicate that 3-deaza-cADPR, like 7-deaza-cADPR, is resistant to hydrolysis.

Figure 6:
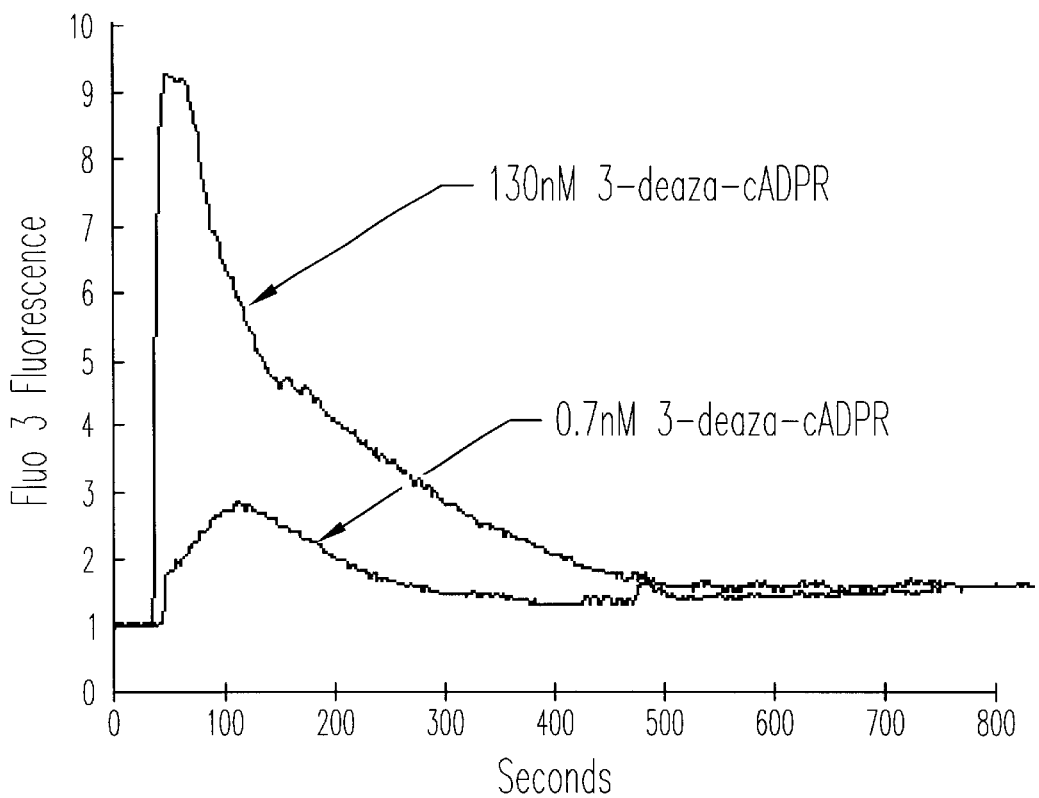
FIG. 6: $Ca^{2+}$ mobilization evoked by microinjection of 3-deaza-cADPR into a live sea urchin egg. The calcium response to injection of two concentrations of 3-deaza-cADPR are shown. The concentrations of 3-deaza-cADPR indicated on the figure correspond to final concentrations in the egg calculated based on the volumes of the egg and injection. The 130 nM 3-deaza-cADPR response was induced by injecting 10 $\mu$M 3-deaza-cADPR in a volume representing 1.3% of the egg volume. The 0.7 nM 3-deaza-cADPR response was induced by injecting 100 nM 3-deaza-cADPR in a volume representing 0.7% of the egg volume.

The ability of 3-deaza-cADPR to mobilize intracellular $Ca^{2+}$ in an intact system was tested. Live L. pictus eggs were preloaded with the calcium indicator, fluo 3, by microinjection. Subsequent injection of 100 nM 3-deaza-cADPR (pipette concentration) induced a small $Ca^{2+}$ transient (FIG. 6). At this level of 3-deaza-cADPR (about 0.7 nM in the egg), 1 out of 6 injected eggs underwent a partial cortical reaction. Increasing the concentration of 3-deaza-cADPR to 1 $\mu$M (about 10 nM in the egg) produced 4 full cortical reactions and 1 partial reaction out of the 7 eggs injected at this concentration. With 10 $\mu$M 3-deaza-cADPR in the pipette (~130 nM in the egg), 5 out of 5 eggs had a full cortical reaction and a large $Ca^{2+}$ transient was evoked (FIG. 6). Therefore, 3-deaza-cADPR exhibits similar potency in live eggs as well as in vitro.

Example 2

Effects of Extracellular cADPR on Human Hemopoietic Progenitors

Materials and Methods

Nucleotides

Cyclic ADP-ribose (cADPR) and [$^3$H]-cADPR were prepared enzymatically from $NAD^+$ and [$^3$H]-$NAD^+$, respectively, with Aplysia californica cyclase (courtesy of Prof. H. C. Lee, Minneapolis, Minn.) and HPLC purified. Recombinant CD38 was kindly provided by Prof. H. C. Lee. 8-$N_3$-$NAD^+$ was synthesized as described (T. Walseth, et al., (1997) Methods Enzymol. 280, 294–300) and reduced to 8-$NH_2$-$NAD^+$ with DTT: 8-$NH_2$-cADPR was then obtained by incubation with Aplysia cyclase and HPLC purified. 3-Deaza-cADPR was synthesized as described (L. Wong, et al., Biochemica and Biophysica Acta vol. 1472, Issue 3, page 555). ADP-ribose (ADPR) was obtained from Sigma, Milan, Italy.

Samples

Cord blood (CB) samples were collected from umbilical cords into tubes containing preservative-free heparin after normal full-term deliveries. Maternal informed consent was obtained in all cases.

Normal bone marrow (BM) cells were obtained from donors providing marrow for allogeneic transplantation. Leukapheresis samples were obtained from normal donors providing peripheral blood (PB) progenitor cells for allogeneic transplant after a short course of granulocyte colony-stimulating factor. All donors gave informed consent. Mononuclear cells (MNC) from CB, BM and PB were separated by density gradient centrifugation on Ficoll-Hypaque (Sigma). After separation, cells were washed twice in Iscove's Modified Dulbecco's Medium (IMDM) containing 5% fetal calf serum (FCS) and resuspended in IMDM containing 10% FCS, penicillin 100 U/ml, streptomycin 100 $\mu$g/ml and glutamine 2 mM (complete medium). The cADPR-hydrolase activity of freshly isolated MNC was assayed as described (Zocchi, E. et al., (1998) J.Biol. Chem., 273, 8017–8024).

CD $34^+$ Cell Enrichment and CD $34^+38^{low}$ Separation

Immunoaffinity purification of $CD34^+$ cells was used to enrich MNC in colony forming cells (CFC) and early progenitors (Krause, D. S., ET AL.,(1996) Blood 87, 1–13). $CD34^+$ cell enrichment was performed by positive selection using the miniMACS immunomagnetic separation system (Miltenyi Biotec GmBH, Germany). Briefly, PB- or CB-derived MNC were suspended in phosphate-buffered saline (PBS) containing 0.5% bovine serum albumin and 5 mM EDTA and $CD34^+$ cells were separated using anti-CD34 antibody (clone: QBEND/10; isotype: mouse IgG1) and colloidal superparamagnetic beads. After labeling, the cell suspension was passed through a column held within a magnetic field causing $CD34^+$ cells to be retained in the column. Purified $CD34^+$ cells were then collected following removal of the column from the magnet and washing with buffer.

Enrichment of the MNC in the earliest HP was obtained by negative selection of the $CD34^+38^{low}$ cells using the StemSep Separation System (StemCell Technologies Inc). Cells were labeled for magnetic depletion by incubation with a cocktail of tetrameric antibody complexes (anti-CD38, CD66b, CD19, CD2, CD45RA, CD16, CD24, CD3, CD36, CD14, CD56, glycophorin A) and magnetic dextran iron particles. The cell suspension was then passed through a high gradient magnetic column of stainless steel mesh. The magnetically labeled cells bind to the column while the unlabeled cells, containing the most immature HP (CD $34^+38^{low}$), pass through: these cells do not have antibodies bound to their surface and are suitable for further functional studies.

Liquid Cultures

Incubations were performed in a total volume of 1 ml complete medium (see above) with $10^6$ MNC/ml for 24 hours in a humidified, 5% $CO_2$ atmosphere at 37° C. cADPR or ADPR (100 $\mu$M final concentration) was added once at the beginning of the incubation period. When the incubation time exceeded 24 hours (2, 5, 9, 15 days) cADPR or ADPR was added twice a week and different tubes were used for each time point.

3-Deaza-cADPR, a non-hydrolyzable cADPR analog, was used under the same culture conditions described above at a final concentration of 1 to 1000 nM and was added only at the beginning of the incubation.

Semisolid Colony Growth Assay

After liquid culture, an appropriate number of MNC or $CD34^+$-enriched cells was plated in methylcellulose medium supplemented with a mixture of hemopoietic growth factors (Methocult; Stem Cell Technologies, Vancouver, BC, Canada). After 14 days of incubation in a humidified, 5% $CO_2$ atmosphere at 37° C., colonies were scored using an inverted microscope, applying standard criteria for their identification.

Thereafter, an appropriate number of the recovered cells (usually 1/30–1/10 from the first generation and 1/10–1/2 from subsequent generations) was replated in complete methylcellulose medium for assessment of the replating efficiency. The total number of CFC grown in each generation (14 days) was calculated by dividing the number of scored colonies by the fraction of the total cell number, recovered from the previous generation(s), that was plated. In each experiment, the sum of the colonies grown throughout the generations from cADPR-primed HP was then divided by the sum obtained in the respective control to calculate the expansion factor.

Cytosine Arabinoside-susceptibility of CB MNC

Cytosine arabinoside (c-ARA) was used to determine the proportion of cycling CFC, as described by Dresch, C., et al., (1983) Exp. Hematol. 11, 187–192. MNC ($10^6$/ml) were incubated at 37° C. in a humidified, 5% $CO_2$ atmosphere for 24 hours in complete medium (containing 20% FCS) with or without 1 $\mu$M c-ARA and subsequently washed twice in IMDM containing 5% FCS. Incubation with or without cADPR (100 $\mu$M) was performed before or after c-ARA treatment, under the liquid culture conditions described above, for 24 hours. Thereafter, cells were washed, counted and plated in semisolid medium for assay of CFC at a concentration of $10^4$ MNC/plate.

Fluorimetric Determination of the $[Ca^{2+}]_i$

CB-derived MNC ($10^7$/ml) were incubated with 6 µM Fura 2 acetoxymethyl ester (FURA 2 AM) in complete culture medium for 45 min at 37° C., washed with standard saline (135 mM NaCl, 5.4 mM KCl, 1 mM $MgCl_2$, 10 mM glucose and 5 mM Hepes, pH 7.4) and resuspended in the same solution at $0.5 \times 10^6$/ml. Measurements were performed at room temperature in a 2 ml-cuvette under continuous stirring. Parameter values for the calculation of the $[Ca^{2+}]_i$ were obtained as described by Zocchi, E. et al., (1998) J.Biol. Chem., 273, 8017–8024. The frequency of recording was 1 point/s.

Due to the small number of $CD34^+/CD38^{+/-}$ cells that can be recovered from CB samples the calcium measurements on these subpopulations were performed on cells settled on glass coverslips (3–4 cells per field), using the same experimental setting described previously (Zocchi, E. et al., (1998) J.Biol. Chem., 273, 8017–8024), except that measurements were performed under conditions of stopped flow. Briefly, 20 µl of FURA 2 AM-loaded cells ($10^6$/ml) were seeded on 20 mm glass coverslips. After 15 min the specimen was mounted in a 200 µl-chamber on the stage of an inverted microscope (Zeiss IM35, Germany) and the chamber was slowly filled with 200 µl of standard saline taking care not to disturb the settled cells.

All measurements were performed in $Ca^{2+}$-free external solutions.

Determination of Intracellular cADPR Concentration

The intracellular cADPR concentration was determined by HPLC analysis on neutralized trichloroacetic acid (TCA) cell extracts. MNC were incubated at $1.5 \times 10^7$/ml in complete medium in the presence of 1 mM cADPR at 37° C. After 10 min, 1 hour or 24 hours, $3 \times 10^7$ cells were washed 4 times in PBS at 25° C.: the cell pellet was resuspended in 300 µl of water, sonicated and TCA extracted. After removal of excess TCA with diethyleter $2 \times 10^3$ cpm of internal standard [$^3$H]cADPR was added to the cell extract, which was subjected to the first HPLC analysis on an anion exchange PL-1000 SAX column (HP, Milan, Italy). An aliquot of each 0.5 min-fraction was counted in a β-counter and the fractions containing the radioactive cADPR standard were pooled, lyophilized and redissolved in 0.5 ml of 20 mM TrisHCl, pH 6.5. Recombinant CD38 (4 µg/ml) was added to one 0.25 ml-aliquot and both samples were incubated at 37° C. for 12 hours. After TCA extraction both incubations were analyzed on a reverse phase Hypersil C18 column (HP, Milan, Italy) and the radioactivity of the 0.3-min fractions was determined. The identity of the cADPR peak in the cell extract was confirmed by co-elution with the radioactive standard, by comparison of the absorbance spectrum with a computer-stored standard and by absence of the corresponding peak in the CD38-hydrolyzed sample. The concentration of intracellular cADPR per $10^8$ cells was calculated from the area of its HPLC peak and taking into account the percentage of nucleotide recovery obtained with the radioactive standard.

Results

Selection of the Protocol for cADPR Treatment

Figure 7:
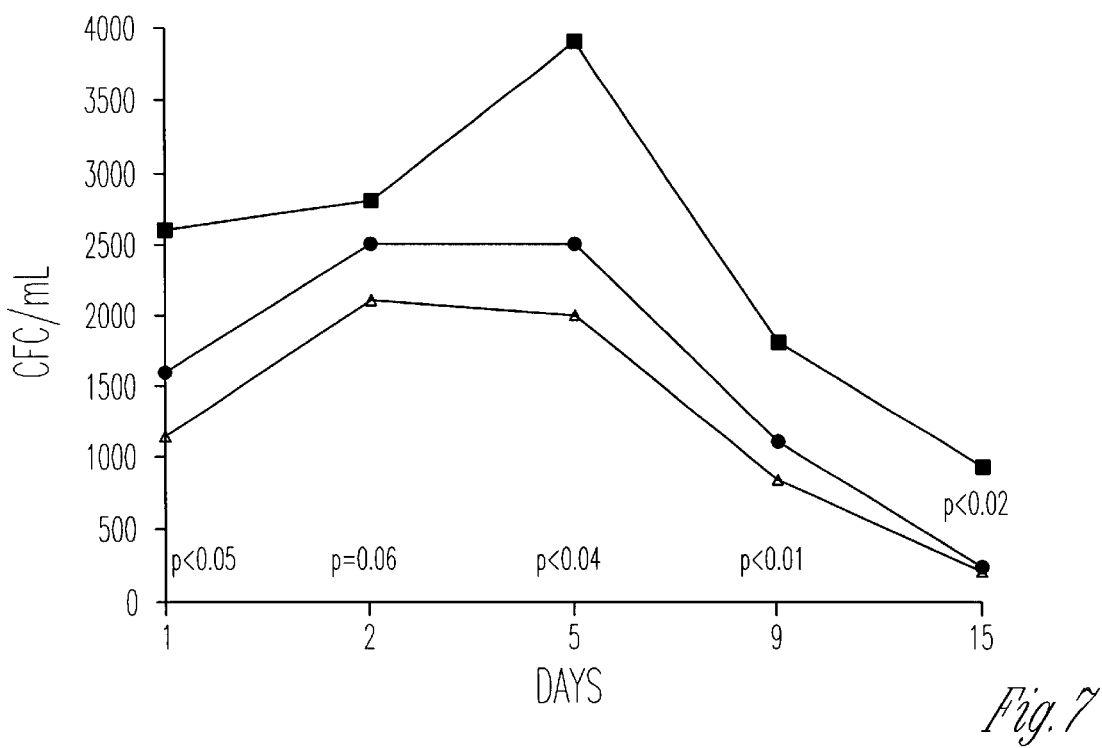
FIG. 7: Colony forming cell (CFC) output of core blood (CB) mononuclear cells (MNC) after different times of cADPR incubation. Cells were cultured in complete medium with or without 100 $\mu$M cADPR or ADPR for the times indicated and subsequently plated in semisolid medium. Results are expressed as CFC number per ml of liquid culture suspension. Each point is the median value of 7–9 experiments. (■), cADPR; (Δ), ADPR; (●), untreated.

To investigate a possible effect of cADPR on the proliferation and on the $[Ca^{2+}]_i$ of hemopoietic progenitors, CB-derived MNC ($10^6$ cells in 1 ml complete medium) were exposed to increasing concentrations of the cyclic nucleotide (1, 10, 100 and 1,000 µM) for 24 hours in liquid culture. Controls were untreated cells, as well as cells incubated with ADPR, i.e. the product of the cADPR-hydrolase activity expressed on the surface of CB MNC. This hydrolase activity (0.014±0.006 nmol/min/$10^6$ cells) would allow extracellularly added cADPR (1, 10, 100 and 1,000 nanomoles) to last approximately 1 hour, 12 hours, 5 days and 50 days, respectively, under the culture conditions described above. Following incubation with cADPR, cells were plated in semisolid medium for assay of CFC number. No effect of ADPR on CFC growth was observed, as compared to untreated cells, at any of the concentrations tested. Conversely, cADPR increased CFC output in a concentration-dependent way, with 100 and 1000 µM inducing a significantly (p<0.01) higher clonogenic growth compared to controls (1,400 and 2,800 vs 700 CFC/ml, respectively; n=3). The lowest cADPR concentrations tested, 1 and 10 µM, were ineffective. The fact that they would be hydrolyzed within 12 hours culture of the cells suggested that 12–24 hours exposure to cADPR was necessary to stimulate cell growth. To test the effect of the length of cADPR exposure on CFC growth, we prolonged the liquid culture up to 15 days: cADPR or ADPR was added every three days to maintain the nucleotide concentration approximately constant. At each time-point (1, 2, 5, 9 and 15 days) cells were counted and plated in semisolid medium. cADPR induced a variable increment of MNC but a remarkable expansion of CFC at all time-points tested (FIG. 7), with the most significant difference between cADPR-treated and control progenitors being recorded after 15 days (p<0.002). However, the net CFC output decreased significantly over time, in control—as well as in cADPR-treated cultures.

Finally, in the absence of growth factors cADPR did not produce any colony growth when directly added to the semisolid medium.

Based on these observations, the protocol for cADPR treatment was devised as follows: the lowest cADPR concentration (100 µM) sufficient to survive degradation by the hydrolase activity of $10^6$ MNC/ml, without the need for repeated additions, and the shortest incubation time necessary to stimulate cell growth (24 hours) were the culture conditions subsequently used.

Stimulatory Effect of cADPR on the Growth of CFC

In all experiments (n=25), extracellular 100 µM cADPR significantly enhanced CFC output from CB MNC: the median was 5,000 CFC/ml (range 720–17,340) compared to ADPR-treated cells, median 2,141 (range 600–13,120; p<0.01), or to untreated cells, median 2,900 (range 450–12,670; p<0.01) (Table 1). The wide range in the absolute numbers reflects the variability of the proliferative capacity of CFC from different CB samples (Cairo, M. S. and Wagner, J. E. (1997) Blood, 90, 4665–4678): however, in each single experiment, cADPR induced a higher CFC output compared to controls (Table 1).

TABLE 1

Stimulation of total colony output by cADPR.

| Experiment n° | Untreated | cADPR | ADPR |
|---|---|---|---|
| 1 | 1,692 | 4,337 | 1,890 |
| 2 | 3,855 | 10,155 | 2,570 |
| 3 | 4,171 | 8,632 | 5,505 |
| 4 | 1,630 | 15,220 | 13,120 |
| 5 | 5,764 | 6,066 | 5,515 |
| 6 | 4,010 | 6,303 | 1,990 |
| 7 | 3,310 | 4,700 | 1,510 |
| 8 | 4,708 | 4,774 | 2,283 |
| 9 | 2,665 | 5,050 | 945 |
| 10 | 3,716 | 3,915 | 3,760 |
| 11 | 1,300 | 3,200 | 2,000 |
| 12 | 4,100 | 5,900 | 3,200 |
| 13 | 2,900 | 3,800 | 2,700 |
| 14 | 1,180 | 1,640 | 1,480 |
| 15 | 5,600 | 6,700 | 5,100 |
| 16 | 1,000 | 2,200 | 1,700 |
| 17 | 1,540 | 3,060 | 1,425 |

TABLE 1-continued

Stimulation of total colony output by cADPR.

| Experiment n° | Untreated | cADPR | ADPR |
|---|---|---|---|
| 18 | 450 | 720 | 600 |
| 19 | 2,670 | 5,000 | n.d. |
| 20 | 3,900 | 4,500 | n.d. |
| 21 | 8,330 | 12,760 | n.d. |
| 22 | 12,670 | 17,340 | n.d. |
| 23 | 2,900 | 4,400 | n.d. |
| 24 | 450 | 4,680 | n.d. |
| 25 | 2,240 | 4,250 | n.d. |
| Median CFC number per ml | 2,900 | 5,000 | 2,141 |
| Range | 450–12,670 | 720–17,340 | 600–13,120 |

Freshly isolated CB MNC were incubated without or with 100 $\mu$M cADPR or ADPR for 24 hours. An aliquot of the cell suspension was then plated in semisolid medium for determination of colony output. The total number of CFC was calculated taking into account the fraction of the liquid culture suspension that was plated. cADPR vs. untreated, $p < 0.01$; cADPR vs. ADPR, $p < 0.01$; ADPR vs. untreated, $p = 0.8$; n.d., not determined.

On the other hand, the number of cells recovered after liquid culture was not significantly higher in cADPR-treated cells compared to controls (cADPR- vs. ADPR- and cADPR- vs. un-treated cells, p=0.4). In order to correlate the functional effect to cADPR itself, we also assayed the non-hydrolyzable cADPR analog, 3-deaza-cADPR, on CFC output. Different concentrations (1, 10, 100 and 1,000 nM) were tested under the same culture conditions described above. 3-deaza-cADPR induced a significant increase of the CFC output compared to control, untreated cells, at each concentration tested (p<0.04): thus, 1 nM of the analog produced 95% of the effect induced by 1 $\mu$M, with medians of 2,050 and 2,200 CFC/ml, respectively, compared to a median of 1,150 obtained with the control (n=5).

The experimental protocol described above ($10^6$ MNC/ml, 100 $\mu$M cADPR for 24 hours) was also tested on bone marrow (BM)-derived and on peripheral blood (PB)-derived clonogenic progenitors. Higher CFC numbers grew from BM (n=3) and from PB (n=2) after cADPR treatment as compared to the respective controls, incubated with ADPR: medians were 2,660 vs. 1,500 for BM-derived and 2,750 vs. 1,460 for PB-derived CFC/ml. These results demonstrate that the effect of cADPR is not restricted to ontogenetically immature (CB-derived) progenitor cells.

Finally, the effect of cADPR treatment on colony size and type was analyzed. Colonies arising from cADPR-primed MNC were significantly larger than ADPR-treated or untreated controls (Table 2, below), this indicating an increased proliferation rate within the single colony.

The increase of CFC output was statistically significant for all colony types, i.e. colony-forming units granulocyte macrophage (CFU-GM) ($\chi^2$=28.5; $\alpha$<0.005), burst-forming units erythroid (BFU-E) ($\chi^2$=27.5; $\alpha$<0.005) and multipotential colony-forming units (CFU-GEMM) ($\chi^2$=7.1; $\alpha$<0.01), indicating a stimulatory effect of cADPR on all hemopoietic lineages.

TABLE 2

Effect of cADPR on colony size.

| Experiment n° | Untreated | cADPR | ADPR |
|---|---|---|---|
| 1 | 8,250 | 11,500 | 6,500 |
| 2 | 16,000 | 30,500 | 19,000 |
| 3 | 13,600 | 39,000 | 16,600 |
| 4 | 9,530 | 27,590 | 18,340 |
| 5 | 10,250 | 25,680 | 12,320 |
| 6 | 8,400 | 12,100 | 6,700 |
| 7 | 11,300 | 21,450 | 10,800 |
| 8 | 7,800 | 9,340 | 6,200 |
| 9 | 8,700 | 14,700 | n.d. |
| 10 | 8,500 | 10,600 | n.d. |
| Median number of cells per colony | 9,135 | 18,075 | 11,560 |
| Range | 7,800–16,000 | 9,340–39,000 | 6,200–19,000 |

After scoring (see legend to Table 1), colonies were recovered and the total cell count was determined. This was divided by the original colony number to obtain the median cell number per colony. cADPR vs. untreated, $p < 0.003$; cADPR vs. ADPR, $p < 0.05$; ADPR vs. untreated, $p = 0.3$; n.d., not determined.

Increased $[Ca^{2+}]_i$ in CB MNC incubated with cADPR or 3-deaza-cADPR

Figure 8:
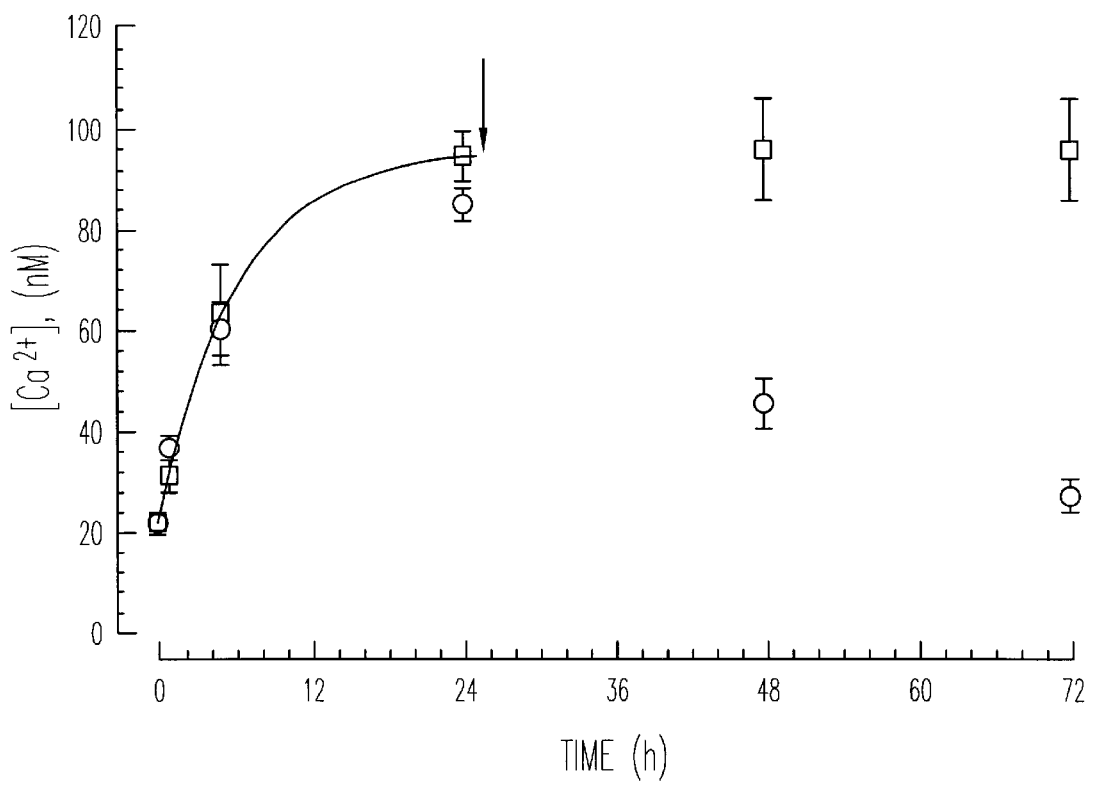
FIG. 8: $[Ca^{2+}]_i$ of CB MNC incubated with cADPR or 3-deaza-cADPR. $[Ca^{2+}]_i$ was determined on FURA 2-loaded cells at different times during incubation with 100 $\mu$M cADPR (○) or 10 nM 3-deaza-cADPR (□) and after 24 and 48 hours following removal of the cyclic nucleotide (arrow). Each point is the mean±s.d. of at least 7 determinations obtained from independent experiments.

The same cADPR and 3-deaza-cADPR concentrations used in the liquid culture experiments described above were tested for their effect on the $[Ca^{2+}]_i$ of CB MNC. The $[Ca^{2+}]_i$ in freshly isolated CB MNC was found to be 20.3±1.8 nM (n=20). Closely comparable values were obtained with cells in suspension or on glass coverslips (see Materials and Methods). Upon incubation with 100 $\mu$M cADPR or 10 nM 3-deaza-cADPR the $[Ca^{2+}]_i$ increased in a time-dependent manner (FIG. 8) up to 82.6±3.4 nM and 96.4±5.0 nM for cASPR and 3-deaza-cADPR, respectively, after 24 hours (n=7). To simulate a constant supply of micromolar cyclic nucleotide, repeated additions of 1–10 $\mu$M cADPR were performed during 24 hours liquid culture: this treatment determined a final $[Ca^{2+}]_i$ increase in the MNC similar to that observed after a single addition of 100 $\mu$M cADPR (not shown). Upon removal of cADPR by repeated washings of the cells, the $[Ca^{2+}]_i$ decreased progressively to 160% and 110% of basal values after 24 and 48 hours, respectively. Calcium levels remained unchanged in 3-deaza-cADPR-treated cells for at least 48 hours following removal of the nucleotide (FIG. 8).

The time-course of the $[Ca^{2+}]_i$ increase in 3-deaza-cADPR-incubated cells (FIG. 8) can be described by the following three-parameter, single exponential regression curve:

$$[Ca^{2+}]_i(t)=[Ca^{2+}]_i(t=0)+\Delta_{max}[Ca^{2+}]_i\{1-\exp(-t/\tau)\}$$

where $[Ca^{2+}]_i(t=0)$ is the intracellular free calcium concentration before incubation, $\Delta_{max}[Ca^{2+}]_i$ is the maximal calcium change and $\tau$ is the time constant of the process, i.e. the time required to reach 65% of the maximal value. The experimental data are best fitted by the parameters: $[Ca^{2+}]_i(t=0)$=21.1±0.6 nM, $\Delta_{max}[Ca^{2+}]_i$=74.0±0.7 nM and $\tau$=6.5 h, with R=0.999 (p<0.0001). This result suggests that the increase of $[Ca^{2+}]_i$ is the result of a single rate-limiting event, described by the curve itself, rather than the sum of multiple steps having different kinetics. Moreover, a time constant of the order of hours strongly suggests a slow influx of the cADPR analog into the cells rather than binding to a hypothetical membrane receptor, followed by signal-transducing events eventually leading to calcium release from internal stores.

Figure 9A:
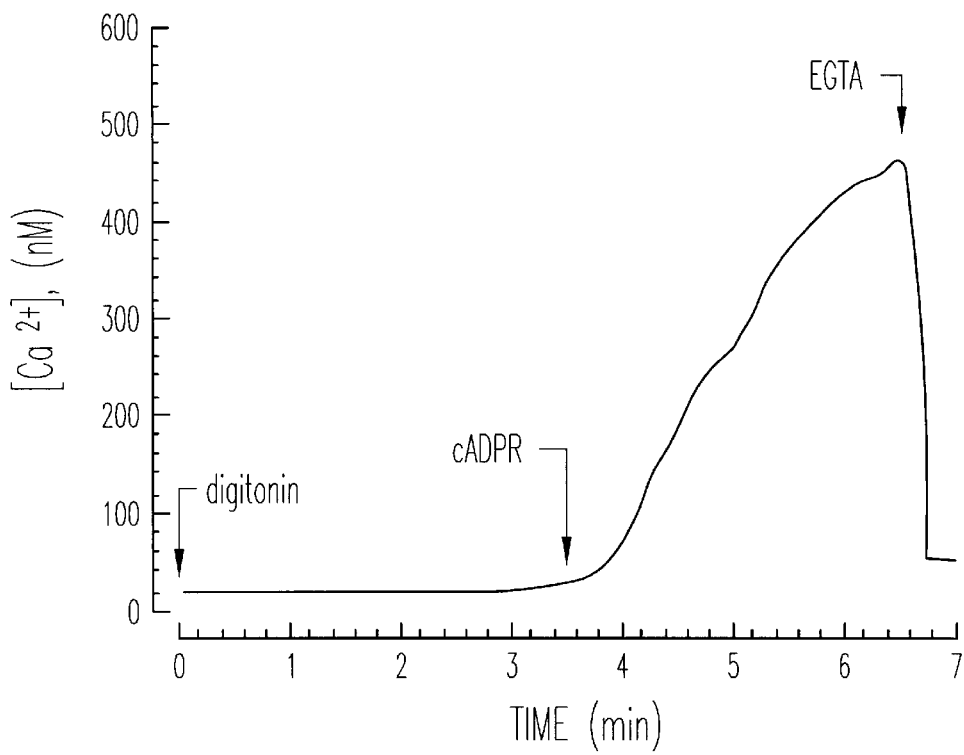
FIGS. 9A and 9B: Time-course of $[Ca^{2+}]_i$ increase in CB MNC exposed to cADPR or 3-deaza-cADPR: effect of cell permeabilization. The $[Ca^{2+}]_i$ was continuously monitored for 30 min following addition (time zero) of 100 $\mu$M cADPR (○) or 10 nM 3-deaza-cADPR (□) to FURA 2-loaded CB MNC suspended in zero-calcium external solution. (Δ), untreated cells. Traces shown are representative of 3 consistent experiments. Each point is the mean of the values (=200) recorded in 2 min.
Figure 9B:
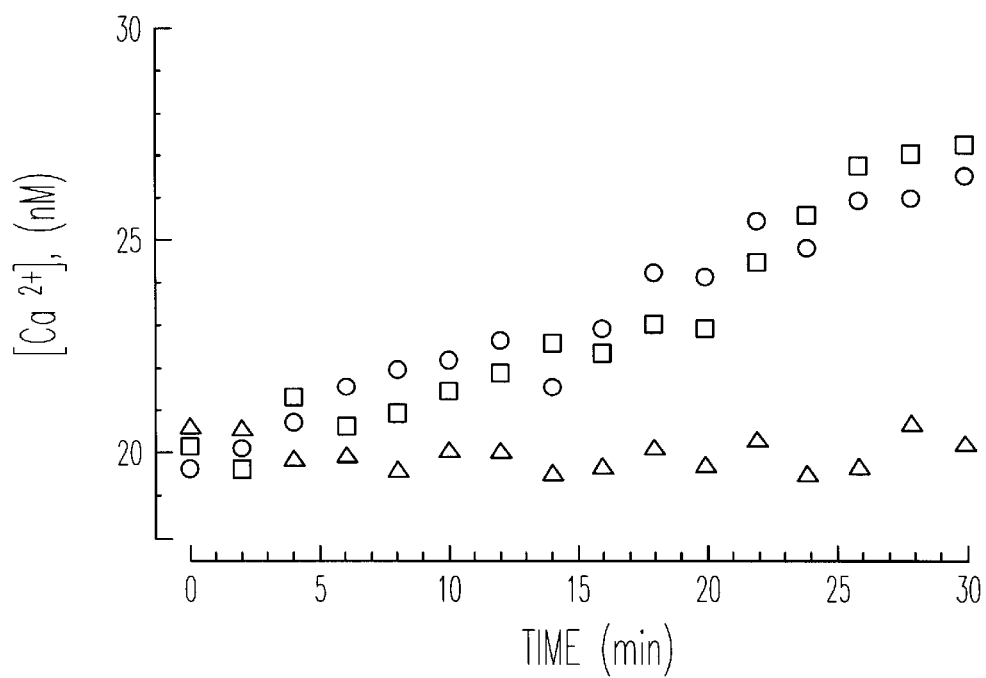

In order to elucidate whether slow cADPR influx across the cell membrane was the rate-limiting event we followed the calcium increase in real time upon addition of cADPR to intact or to permeabilized MNC cells. While addition of 100 $\mu$M cADPR to digitonin-permeabilized cells elicited an immediate and considerable calcium release (FIG. 9A), intact cells responded with a slow and progressive increase of $[Ca^{2+}]_i$ detectable over a 30-min time span (FIG. 9B). The same rate and extent of calcium increase were observed upon addition of 10 nM 3-deaza-cADPR (FIG. 9). The fact that these calcium increases were obtained in zero-calcium external solutions rules out any influx of extracellular $Ca^{2+}$.

Determination of Intracellular cADPR Concentration

In order to achieve direct evidence for cADPR influx across the cell membrane, we investigated the presence of the cyclic nucleotide in TCA extracts of MNC cultured in the presence of 1 mM cADPR for different times. No cADPR was detectable in extracts of cells incubated with cADPR for 10 min, indicating that the repeated washings of the cells were adequate to remove all extracellular and/or surface-bound nucleotide. After 1 hour incubation of the cells with cADPR, however, the cyclic nucleotide became detectable in cell extracts and after 24 hours its intracellular concentration was 0.55±0.16 nanomoles/$10^8$ cells. These values are in the range of reported intracellular cADPR concentrations in $CD38^+$ human lymphoid and myeloid cell lines (Takabashi, K., et al., (1995) FEBS Lett. 371, 204–208; and da Silva, C., et al.,(1998) J. Chromatogr. B 707, 43–50).

Inhibitory Effect of cADPR Antagonists on CFC Growth and on $[Ca^{2+}]_i$

In an attempt to causally correlate the increase of $[Ca^{2+}]_i$ with the growth-promoting effect induced by cADPR, CB MNC were incubated with a specific cADPR antagonist, 8-$NH_2$-cADPR, prior to exposure to cADPR. Interestingly, pre-treatment of the cells with 8-$NH_2$-cADPR (10 µM) for 24 hours, while not affecting cell viability during the liquid culture, completely inhibited colony growth in the subsequent two weeks, eventually leading to cell death in the semisolid medium: the median was zero CFC/ml (no growth was ever observed) compared to a median of 3,400 (range 2,000–3,800) for untreated controls (n=3). Prolonging the liquid culture for further 24 hours with the addition of cADPR (100 µM) did not restore colony growth. However, presence of a 10- or 100-fold excess of cADPR (100 µM or 1 mM) together with 10 µM 8-$NH_2$-cADPR in the liquid cultures for 24 hours reduced or abolished, respectively, the inhibitory effect of the cADPR antagonist on colony growth. Mean values, calculated from closely comparable results, were 2,800, zero and 1,200 CFC/ml for control, 8-$NH_2$-cADPR and 8-$NH_2$-cADPR plus 10-fold excess cADPR (n=3) and 2,600, zero and 2,500 CFC/ml for control, 8-$NH_2$-cADPR and 8-$NH_2$-cADPR plus 100-fold excess cADPR (n=3), respectively. Similar results, in terms of cADPR-induced recovery from inhibition of colony growth, were obtained with another cADPR antagonist, 8-$N_3$-cADPR.

Incubation of the cells with 10 µM 8-$NH_2$-cADPR for 24 hours resulted in a significant decrease of the basal $[Ca^{2+}]_i$ from 20±2 to 14±1 nM (n=3) and in a consistent increase of the amount of $Ca^{2+}$ releasable by the calcium ionophore A23187, compared to untreated control cells, indicating an increased repletion state of microsomal stores in 8-$NH_2$-cADPR-treated cells.

Moreover, 8-$NH_2$-cADPR completely inhibited the calcium-releasing activity of cADPR on CB MNC. Specifically, pre-incubation of the intact cells for 2 hours in the presence of 100 µM 8-$NH_2$-cADPR completely inhibited the calcium increase induced by the subsequent addition of 100 µM cADPR for 4 hours: the $[Ca^{2+}]_i$ values measured following exposure to cADPR were 20 nM in the in 8-$NH_2$-cADPR-preincubated and 58 nM in the untreated cells (n=2).

Stimulatory Effect of cADPR on Growth and on $[Ca^{2+}]_i$ of $CD34^+$-enriched MNC To minimize a possible influence of accessory cells in mediating the stimulation of CFC growth by cADPR, the effect of the cyclic nucleotide was tested on $CD34^+$-enriched fractions ($10^6$ cells/ml) derived either from PB (n=2) or from CB (n=2). The $CD34^+$ subpopulation, representing 0.1–0.5% of the total nucleated cells derived from PB or CB, contains the earliest and committed precursors for all hemopoietic lineages. A stimulatory effect of cADPR (100 µM for 24 hours) was observed on the growth of CFC from these HP-enriched subpopulations: cADPR-treated (median 121,000 CFC/$10^6$ MNC, range 1,800–151,000) vs ADPR-treated (median 18,000, range 360–70,000, p<0.01) and untreated cells (median 16,000, range 800–23,000, p<0.01) (n=6). In parallel, the effect of cADPR on the $[Ca^{2+}]_i$ of $CD34^+$ MNC from CB was investigated: the kinetics of calcium increase following addition of 100 µM cADPR to cells settled on glass coverslips, as monitored in real time on 3–4 cells per field, closely paralleled those of total MNC shown in FIG. 9. Incubation with 100 µM cADPR for 24 hours resulted in an increase of the $[Ca^{2+}]_i$ from 20 nM to 81 nM and to 93 nM in $CD34^+/38^+$ and $CD34^+/38^{low}$ subpopulations, respectively (mean of 2 experiments, giving closely comparable results). Moreover, the $[Ca^{2+}]_i$ remained unchanged in $CD34^+/38^{low}$ MNC for at least 24 hours following removal of external cADPR through repeated washings, in agreement with the lack of hydrolase activity in this MNC subpopulation.

Increased Replating Efficiency of cADPR-primed Hemopoietic Progenitors

To assess whether a short exposure to cADPR (100 µM for 24 hours) might have long-term effects on hemopoietic progenitors, the replating efficiency of cADPR-primed CB MNC was examined. Indeed, cADPR-primed progenitors were found to be able to grow for multiple generations (up to 4) when replated, while control, untreated cells never produced any colony beyond the second generation. The expansion factor (see "Materials and Methods") for cADPR-primed CFC compared to control was calculated to be between 10 and 700 (Table 3, below).

Figure 10A:
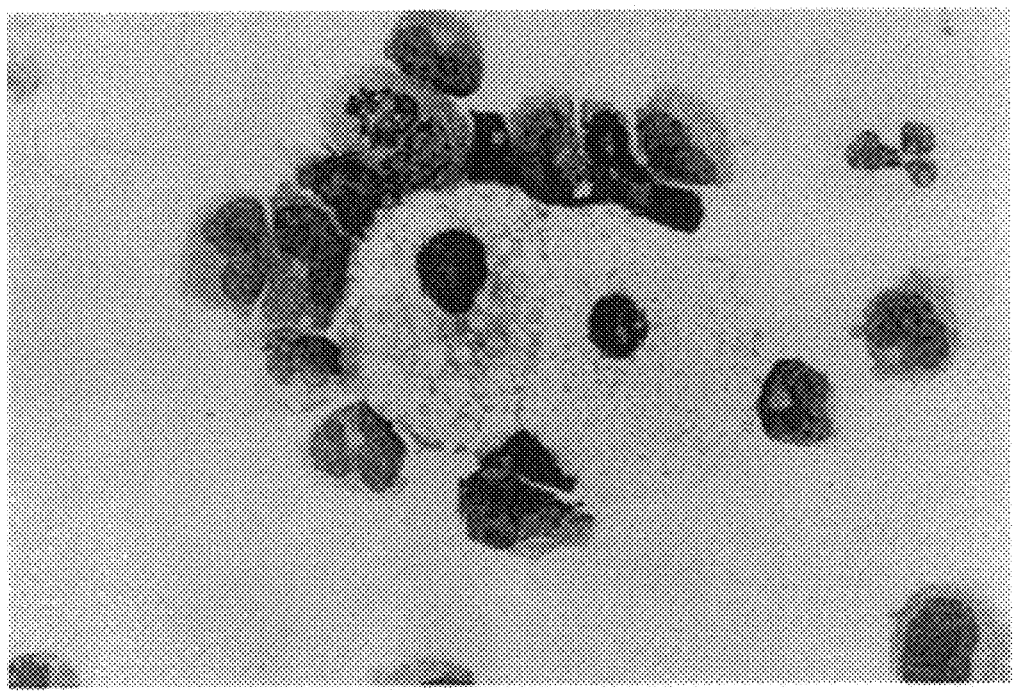
FIGS. 10A and 10B: Secondary cord blood cultures: cytological characteristics of cADPR-primed and control cells. Second-generation colonies grown from cADPR-primed (100 $\mu$M for 24 hours) or control (untreated) CB MNC were pooled and an aliquot of the cells was stained with May-Grünwald Giemsa. The rest of the cells was plated again in semisolid medium: while no further colony growth was observed in the control, cADPR-primed cells produced third- and fourth-generation colonies in the subsequent 5 weeks. (A), cells from cADPR-primed colonies, showing two differentiated macrophages surrounded by a number of smaller, undifferentiated cells; (B), cells from untreated, control colonies. Original magnification: 600×.
Figure 10B:
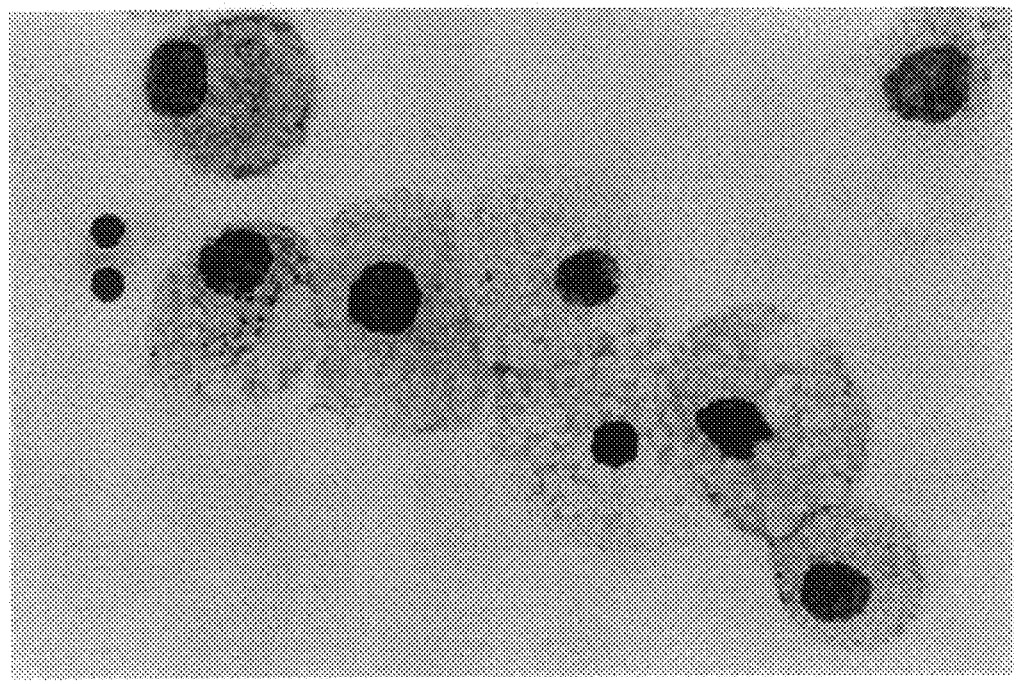

Moreover, second generation colonies arising from cADPR-primed (100 µM for 24 hours) MNC were found to contain mostly elements with the morphology of undifferentiated cells: indented nucleus with sharp chromatin and high nuclear/cytoplasmic ratio. On the contrary, the majority of the cells from control second-generation colonies were terminally differentiated, mature macrophages with foaming cytoplasms and pyknotic nuclei (FIG. 10).

TABLE 3

Increased replating efficiency following cADPR-priming of CB MNC.

| | | generations | | | |
|---|---|---|---|---|---|
| Experiment n° | | 1 | 2 | 3 | 4 |
| 1 | control | 15 | 465 | 0 | 0 |
| | cADPR | 19 | 972 | 1,755 | 1,404 |
| 2 | control | 11 | 617 | 0 | 0 |
| | cADPR | 15 | 530 | 1,480 | 61,670 |
| 3 | control | 5 | 24 | 0 | 0 |
| | cADPR | 8 | 88 | 500 | 0 |
| 4 | control | 9 | 0 | 0 | 0 |
| | cADPR | 17 | 100 | 6,400 | 0 |
| 5 | control | 4 | 180 | 0 | 0 |
| | cADPR | 8 | 520 | 5,000 | 0 |
| 6 | control | 17 | 80 | 0 | 0 |
| | cADPR | 22 | 240 | 10,000 | 0 |

After incubation with or without (control) 100 µM cADPR for 24 hours, CB MNC ($10^4$) were plated in semisolid medium. After 14 days, first generation colonies were scored and a fraction of the recovered cells was replated. Results are expressed as the total number of CFC grown in each generation per $10^4$ MNC seeded in the first one. No colony growth was observed beyond the fourth generation in cADPR-primed MNC.

Cytosine Arabinoside-susceptibility of the cADPR-sensitive CFC

In order to characterize the cycling status of the cADPR target cells in the CFC assay, the sensitivity of the cADPR-sensitive cells to c-ARA was evaluated. When c-ARA pre-treated CB MNC (1 μM for 24 hours) were incubated with cADPR (100 μM for 24 hours), the colony number was not significantly different from controls, incubated without cADPR: the corresponding medians were 18 vs 21 per $10^4$ plated MNC, p=0.7 (n=8). Conversely, the colony number after cADPR incubation alone was significantly higher compared to controls (39 vs $23/10^4$ MNC; p<0.02) and to colonies exposed to c-ARA followed by cADPR (39 vs $18/10^4$ MNC; p<0.004). Similar results (i.e. complete inhibition of the growth-stimulating effect of cADPR by c-ARA) were obtained when cADPR-treatment preceded c-ARA incubation (not shown). Thus, in the liquid culture conditions used for the CFC assays (100 μM cADPR for 24 hours), the cADPR-sensitive cell is cycling, i.e. c-ARA-sensitive. The c-ARA pretreatment of CB MNC (1 μM for 24 hours) did not affect the increased replating efficiency produced by cADPR priming and recorded over several weeks (not shown).

cADPR. *L. pictus* homogenates were used in the binding study because they have much higher binding capacity than those from *S. purpuratus*.

All U.S. Patents cited herein, particularly including U.S. Pat. Nos. 5,486,604 and 5,872,243, and U.S. provisional application No. 60/161,820, are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

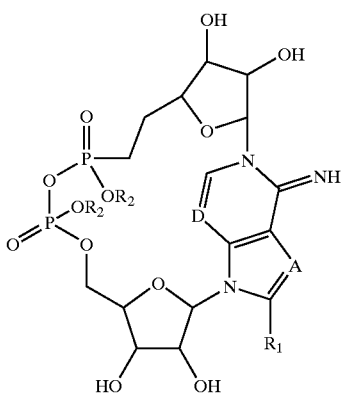

wherein:
A is —N═, or —C(H)═;
D is —C(H)═;
$R_1$ is hydrogen, amino, azido, or halo; and
each $R_2$ is independently hydrogen, or a suitable photolabile caging group;
or a salt or a detectably labeled derivative thereof.

2. The compound of claim 1 wherein $R_1$ is hydrogen.
3. The compound of claim 1 wherein $R_1$ is amino.
4. The compound of claim 1 wherein $R_1$ is azido.
5. The compound of claim 1 wherein $R_1$ is halo.
6. The compound of claim 1 wherein $R_1$ is hydrogen, amino, azido, or bromo.
7. The compound of claim 1 wherein each $R_2$ is hydrogen.
8. The compound of claim 1 wherein one $R_2$ is hydrogen and the other is a photolabile caging group.
9. The compound of claim 1 wherein the photolabile caging group is an ortho-nitrobenzyl group.
10. The compound of claim 1 which is a detectably labeled derivative.
11. The compound of claim 10 wherein the detectably labeled derivative has one or more $^{32}P$.
12. The compound of claim 10 wherein the detectably labeled derivative has one or more $^{33}P$.
13. The compound of claim 10 wherein the detectably labeled derivative has one or more $^{14}C$.
14. The compound of claim 10 wherein the detectably labeled derivative has one or more $^3H$.
15. A method to promote the proliferation of a hemopoietic progenitor cell comprising contacting the cell with a compound of formula I:

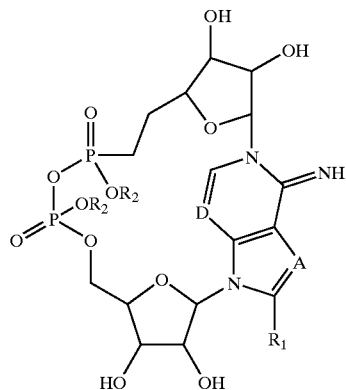

wherein:
A is —N═, or —C(H)═;
D is —N═, or —C(H)═;
$R_1$ is hydrogen; and
each $R_2$ is independently hydrogen, or a suitable photolabile caging group;
or a salt or a detectably labeled derivative thereof.

16. A method to mobilize intracellular calcium in a cell comprising contacting the cell with a compound of formula I:

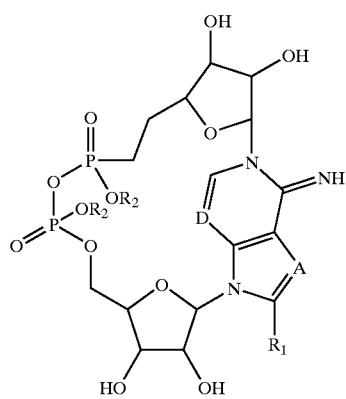

wherein:
A is —N═, or —C(H)═;
D is —C(H)═;

R$_1$ is hydrogen; and each R$_2$ is independently hydrogen, or a suitable photolabile caging group;

or a salt or a detectably labeled derivative thereof.

17. A method to antagonize cADPR induced calcium release in a cell comprising contacting the cell with a compound of formula I:

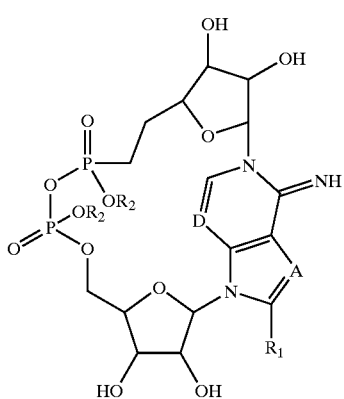

wherein:

A is —N═, or —C(H)═;

D is —C(H)═;

R$_1$ is amino, azido, or halo; and each R$_2$ is independently hydrogen, or a suitable photolabile caging group;

or a salt or a detectably labeled derivative thereof.

18. The method of claim 17 wherein R$_1$ is amino.

19. A method to promote the proliferation of a lymphocyte comprising contacting the lymphocyte with a compound of formula I:

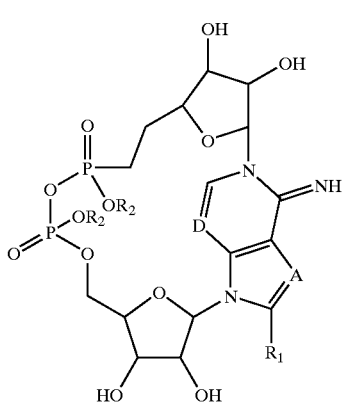

wherein:

A is —N═, or —C(H)═;

D is —N═, or —C(H)═;

R$_1$ is hydrogen; and each R$_2$ is independently hydrogen, or a suitable photolabile caging group;

or a salt or a detectably labeled derivative thereof.

20. The method of claim 19 wherein the lymphocyte is a T-lymphocyte or a B-lymphocyte.

21. A method to enhance the immune system of a mammal comprising administering to a mammal in need of such treatment, an amount of a compound formula I:

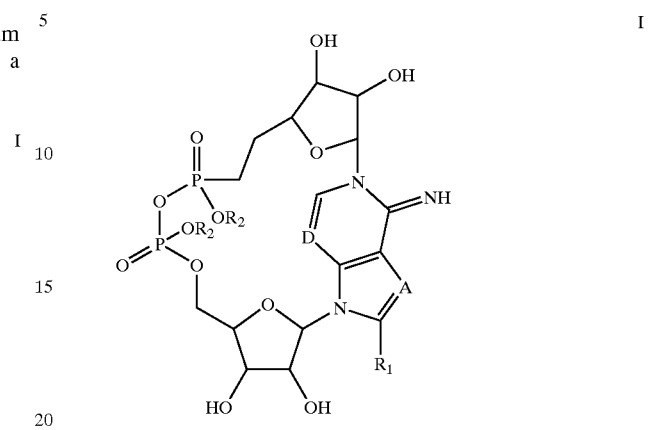

wherein:

A is —N═, or —C(H)═;

D is —N═, or —C(H)═;

R$_1$ is hydrogen; and or a pharmaceutically acceptable salt thereof; effective to promote the proliferation of lymphocytes.

22. The method of claim 21 further comprising administering the compound in combination with another immune enhancing therapy.

23. A method to improve immune system function in a mammal comprising administering to a mammal in need of such therapy an amount of a compound of formula I:

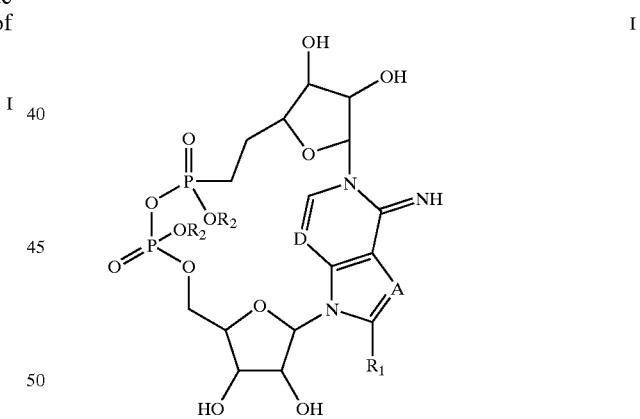

wherein:

A is —N═, or —C(H)═;

D is —N═, or —C(H)═;

R$_1$ is hydrogen; and each R$_2$ is independently hydrogen, or a suitable photolabile caging group;

or a pharmaceutically acceptable salt thereof; effective to promote the proliferation of lymphocytes.

24. The method of claim 23 wherein the immune system function is compromised by AIDS.

* * * * *

UNITED STATES PATENT AND TRADEMARK OFFICE
CERTIFICATE OF CORRECTION

PATENT NO.    : 6,593,307 B1
DATED         : July 15, 2003
INVENTOR(S)   : Timothy F. Walseth et al.

It is certified that error appears in the above-identified patent and that said Letters Patent is hereby corrected as shown below:

Title page,
Item [75], Inventors, delete "Genoa" (all occurrences) and insert -- Genova -- therefor.
Item [57], ABSTRACT,
Delete formula I and insert the following as formula I:

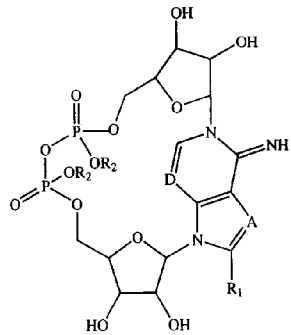

Columns 19-22,
In claims 1, 15, 16, 17, 19, 21 and 23, delete formula I and insert the following as formula I:

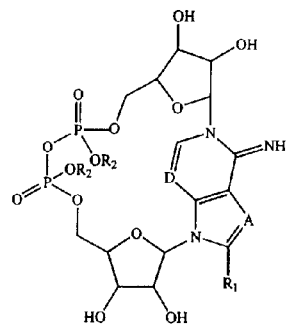

UNITED STATES PATENT AND TRADEMARK OFFICE
CERTIFICATE OF CORRECTION

PATENT NO. : 6,593,307 B1
DATED : July 15, 2003
INVENTOR(S) : Timothy F. Walseth et al.

It is certified that error appears in the above-identified patent and that said Letters Patent is hereby corrected as shown below:

Column 22,
Line 26, insert -- each R2 is independently hydrogen, or a suitable photolabile caging group; -- after "$R_1$ is hydrogen; and".

Signed and Sealed this

Ninth Day of March, 2004

JON W. DUDAS
*Acting Director of the United States Patent and Trademark Office*